(12) United States Patent
Yanagisawa et al.

(10) Patent No.: US 7,417,052 B2
(45) Date of Patent: Aug. 26, 2008

(54) PHENYLENE DERIVATIVE HAVING TETRAZOLE RING OR THIAZOLIDINEDIONE RING

(75) Inventors: Hiroaki Yanagisawa, Tokyo (JP); Yoshiya Amemiya, Tokyo (JP); Kiyoshi Kurokawa, Tokyo (JP); Toshio Miyata, Isehara (JP)

(73) Assignees: Sankyo Company, Limited, Tokyo (JP); RenaScience Co., Ltd., Yokohama (JP)

( * ) Notice: Subject to any disclaimer, the term of this patent is extended or adjusted under 35 U.S.C. 154(b) by 0 days.

(21) Appl. No.: 10/573,274

(22) PCT Filed: Sep. 29, 2004

(86) PCT No.: PCT/JP2004/014684

§ 371 (c)(1),
(2), (4) Date: Jul. 7, 2006

(87) PCT Pub. No.: WO2005/030737

PCT Pub. Date: Apr. 7, 2005

(65) Prior Publication Data

US 2007/0105846 A1    May 10, 2007

(30) Foreign Application Priority Data

Sep. 30, 2003   (JP)   ............... 2003-340007

(51) Int. Cl.
| | |
|---|---|
| A01N 43/42 | (2006.01) |
| A61K 31/44 | (2006.01) |
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |

(52) U.S. Cl. ..................... 514/300; 546/118

(58) Field of Classification Search ............... 546/118; 514/300
See application file for complete search history.

(56) References Cited

U.S. PATENT DOCUMENTS

2002/0099013 A1*   7/2002   Piccariello et al. ............ 514/12

FOREIGN PATENT DOCUMENTS

| JP | 10-310524 A | 11/1998 |
|---|---|---|
| JP | 2002-255813 A | 9/2002 |
| WO | WO 02/083127 A1 | 10/2002 |

OTHER PUBLICATIONS

Jenkins et al., *Expert Opinion on Investigational Drugs* (2002), 11(9), 1205-1223.*
Dannley et al., *Canadian Journal of Chemistry*, 43: 2610-2612 (1965).
Kim et al., *Korean Journal of Medicinal Chemistry*, 5(1): 28-37 (1995).
Lewis et al., *The New England Journal of Medicine*, 329(20): 1456-1462 (Nov. 11, 1993).
Ueno, *Japanese Journal of Clinical Medicine* (*Nippon Rinsho*), 60(10): 1999-2004 (Oct. 1, 2002).
Yamamoto et al., *Chem. Pharm. Bull.*, 46(11): 1716-1723 (Nov. 1998).

* cited by examiner

*Primary Examiner*—D. Margaret Seaman
*Assistant Examiner*—Niloofar Rahmani
(74) *Attorney, Agent, or Firm*—Leydig, Voit & Mayer, Ltd.

(57) ABSTRACT

The present invention provides a compound represented by the following formula (I)

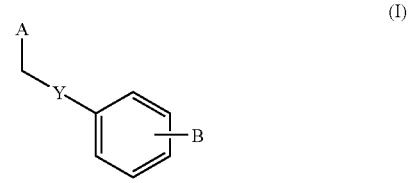

wherein A is a cyclic group etc., B is a 1H-tetrazol-5-yl group or a 2,4-dioxothiazolidin-5-yl group, and Y is a single bond or a C6-10 arylene group, or a pharmacologically acceptable salt thereof or an ester thereof.

13 Claims, No Drawings

PHENYLENE DERIVATIVE HAVING TETRAZOLE RING OR THIAZOLIDINEDIONE RING

TECHNICAL FIELD

The present invention relates to a novel phenylene derivative, a pharmacologically acceptable salt thereof and a pharmacologically acceptable ester thereof. More particularly, the present invention relates to a phenylene derivative having an advanced glycation end products (AGEs) formation inhibitory action and the like, a pharmacologically acceptable salt thereof and a pharmacologically acceptable ester thereof. Furthermore, the present invention relates to an agent for the prophylaxis or treatment of diabetic complications (particularly nephropathy), which comprises a phenylene derivative or a pharmacologically acceptable salt thereof or a pharmacologically acceptable ester thereof as an active ingredient. Moreover, the present invention relates to an agent for the prophylaxis or treatment of the above-mentioned diseases, which comprises the above-mentioned compound as an active ingredient, a composition for the prophylaxis or treatment of the above-mentioned diseases, which comprises the above-mentioned compound as an active ingredient, use of the above-mentioned compound for the production of a medicament for the prophylaxis or treatment of the above-mentioned diseases, and a method for the prophylaxis or treatment of the above-mentioned diseases, which comprises administering a pharmacologically effective amount of the above-mentioned compound to warm-blooded animals (preferably human).

BACKGROUND ART

Conventionally, medicaments having a renoprotective effect (suppression of proteinuria, suppression of renal hypofunction) have been used for the treatment of diabetic nephropathy. Of such medicaments, only the antihypertensive agents of angiotensin II receptor blocker (ARB) and angiotensin converting enzyme inhibitor (ACEI) showed efficacy in large scale clinical trials (New England Journal of Medicine (GB), vol. 329, pp. 1456-1462 (1993)). Since ARB and ACEI have a hypotensive action, their usefulness for patients without hypertension has not been clarified, and suppression of progress of diabetic nephropathy only with the current medicaments is considered to be difficult. Therefore, the development of a potent renoprotective agent free of hypotensive action has been strongly demanded.

In the meantime, AGEs have been known to result from modification of protein by a reactive carbonyl compound produced due to hyperglycemia and oxidative stress in the lesion of diabetic nephropathy. Recently, it has been proved that several kinds of medicaments of ARB and ACEI inhibit formation of AGEs, and the renoprotective effect of ARB and ACEI is exerted independent of the hypotensive action. In addition, it has also been clarified that renal disorder depends on the amount of AGEs contained in the kidney tissue rather than the blood pressure, and that the administration of ARB decreases the amount of AGEs as well as the renoprotective effect.

From the foregoing, since the amount of AGEs contained in kidney tissue could be a significant index of disorder in diabetic nephropathy, the development of a medicament that specifically inhibits AGEs formation is considered to lead to the production of a powerful renoprotective agent free of a hypotensive action.

WO02/083127 discloses a compound having a partially common structure with the phenylene derivative of the present invention, and showing an AGEs formation inhibitory action. However, the compound is different from the compound of the present invention in that a biphenyltetrazole skeleton is essential.

In addition, JP-A-10-310524 discloses a compound having a partially common structure with the phenylene derivative of the present invention, and showing a nephritis inhibitory action. However, the compound is different from the compound of the present invention in that a biphenyltetrazole skeleton is essential and it has an angiotensin II receptor antagonistic action.

DISCLOSURE OF THE INVENTION

The present inventors have conducted intensive studies in an attempt to develop a superior agent for the prophylaxis or treatment of diabetic complications (particularly nephropathy), which is free of a hypotensive action and side effects, and found that a novel phenylene derivative has a superior AGEs formation inhibitory action and improves diabetic complications (particularly nephropathy), which resulted in the completion of the present invention.

Accordingly, the present invention provides a phenylene derivative useful as an agent for the prophylaxis or treatment of diabetic complications and the like, a pharmacologically acceptable salt thereof and a pharmacologically acceptable ester thereof.

Accordingly, the present invention relates to (1) a compound represented by the formula (I)

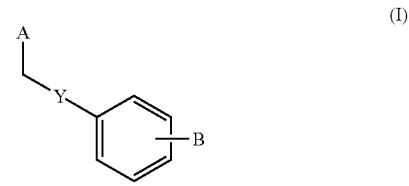

wherein

A is a group represented by the following formula (A1), (A2) or (A3)

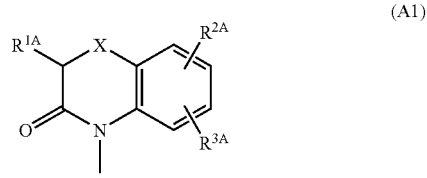

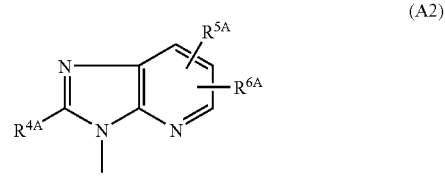

-continued

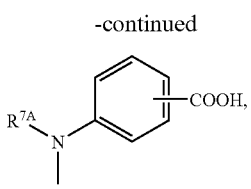
(A3)

B is a 1H-tetrazol-5-yl group or a 2,4-dioxothiazolidin-5-yl group,
X is methylene, an oxygen atom or a sulfur atom,
Y is a single bond or a C6-10 arylene group,
$R^{1A}$ is a hydrogen atom or a C1-6 alkyl group,
$R^{2A}$ and $R^{3A}$ are the same or different and each is a hydrogen atom, a carboxyl group or a C1-6 alkyl group,
$R^{4A}$, $R^{5A}$ and $R^{6A}$ are the same or different and each is a hydrogen atom or a C1-6 alkyl group, and
$R^{7A}$ is a C1-10 alkyl carbonyl group,
provided that when A is (A2), then B should be a 2,4-dioxothiazolidin-5-yl group,
or a pharmacologically acceptable salt thereof or an ester thereof, (2) the compound of the above-mentioned (1), wherein B is a 1H-tetrazol-5-yl group, or a pharmacologically acceptable salt thereof or an ester thereof, (3) the compound of the above-mentioned (1) or (2), wherein Y is a C6-10 arylene group, or a pharmacologically acceptable salt thereof or an ester thereof, (4) the compound of any of the above-mentioned (1) to (3), wherein Y is a phenylene group, or a pharmacologically acceptable salt thereof or an ester thereof, (5) the compound of the above-mentioned (1), wherein B is a 2,4-dioxothiazolidin-5-yl group, or a pharmacologically acceptable salt thereof or an ester thereof, (6) the compound of the above-mentioned (1), wherein A is a group represented by (A1), and B is a 1H-tetrazol-5-yl group, or a pharmacologically acceptable salt thereof or an ester thereof, (7) the compound of the above-mentioned (1), wherein A is a group represented by (A2), and B is a 2,4-dioxothiazolidin-5-yl group, or a pharmacologically acceptable salt thereof or an ester thereof, (8) a compound represented by the formula (IA3)

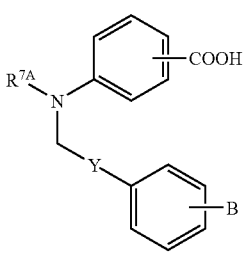
(IA3)

wherein
B is a 1H-tetrazol-5-yl group or a 2,4-dioxothiazolidin-5-yl group,
Y is a single bond or a C6-10 arylene group, and
$R^{7A}$ is a C1-10 alkyl carbonyl group, or a pharmacologically acceptable salt thereof or an ester thereof, (9) the compound of the above-mentioned (8), wherein B is a 1H-tetrazol-5-yl group, or a pharmacologically acceptable salt thereof or an ester thereof,

(10) a compound selected from the group consisting of 3-[N-[[4-[2-(1H-tetrazol-5-yl)phenyl]phenyl]methyl]-N-pentanoylamino]benzoic acid,
3-[N-[[4-[2-(1H-tetrazol-5-yl)phenyl]phenyl]methyl]-N-butanoylamino]benzoic acid,
3-[N-[[4-[2-(1H-tetrazol-5-yl)phenyl]phenyl]methyl]-N-heptanoylamino]benzoic acid,
2-oxo-3-propyl-1-[[4-[2-(1H-tetrazol-5-yl)phenyl]phenyl]methyl]-1,3,4-trihydroquinoline-7-carboxylic acid and
5-[4-[(2-ethyl-5,7-dimethylimidazo[4,5-b]pyridin-3-yl)methyl]phenyl]-1,3-thiazolidine-2,4-dione,
or a pharmacologically acceptable salt thereof or an ester thereof,

(11) 3-[N-[4-(2,4-dioxothiazolidin-5-yl)benzyl]-N-pentanoylamino]benzoic acid, 3-[N-[[4-[2-(1H-tetrazol-5-yl)phenyl]phenyl]methyl]-N-octanoylamino]benzoic acid, or a pharmacologically acceptable salt thereof or an ester thereof,

(12) a medicament comprising the compound of any of the above-mentioned (1) to (11), or a pharmacologically acceptable salt thereof or an ester thereof,

(13) an inhibitor of AGEs formation, which comprises the compound of any of the above-mentioned (1) to (11), or a pharmacologically acceptable salt thereof or an ester thereof,

(14) a pharmaceutical composition for the prophylaxis or treatment of diabetic complication, which comprises the compound of any of the above-mentioned (1) to (11), or a pharmacologically acceptable salt thereof or an ester thereof,

(15) a pharmaceutical composition for the prophylaxis or treatment of diabetic nephropathy, which comprises the compound of any of the above-mentioned (1) to (11), or a pharmacologically acceptable salt thereof or an ester thereof,

(16) use of the compound of any of the above-mentioned (1) to (11), or a pharmacologically acceptable salt thereof or an ester thereof, for the production of a medicament for the prophylaxis or treatment of diabetic complication,

(17) use of the compound of any of the above-mentioned (1) to (11), or a pharmacologically acceptable salt thereof or an ester thereof, for the production of an inhibitor of AGEs formation,

(18) use of the compound of any of the above-mentioned (1) to (11), or a pharmacologically acceptable salt thereof or an ester thereof, for the production of a pharmaceutical composition for the prophylaxis or treatment of diabetic complication,

(19) use of the compound of any of the above-mentioned (1) to (11), or a pharmacologically acceptable salt thereof or an ester thereof, for the production of a pharmaceutical composition for the prophylaxis or treatment of diabetic nephropathy,

(20) a method of inhibiting AGEs formation in a warm-blooded animal, which comprises administering a pharmacological effective amount of the compound of any of the above-mentioned (1) to (11), or a pharmacologically acceptable salt thereof or an ester thereof, to the warm-blooded animal,

(21) a method of preventing or treating diabetic complication in a warm-blooded animal, which comprises administering a pharmacological effective amount of the compound of any of the above-mentioned (1) to (11), or a pharmacologically acceptable salt thereof or an ester thereof, to the warm-blooded animal,

(22) a commercial package comprising the medicament of the above-mentioned (12), and a written matter associated therewith, the written matter stating that the medicament can or should be used for the prophylaxis or treatment of diabetic nephropathy,

(23) a commercial package comprising the inhibitor of the above-mentioned (13), and a written matter associated therewith, the written matter stating that the inhibitor can or should be used for inhibiting AGEs formation,

(24) a commercial package comprising the pharmaceutical composition of the above-mentioned (14), and a written matter associated therewith, the written matter stating that the pharmaceutical composition can or should be used for the prophylaxis or treatment of diabetic complication, and

(25) a commercial package comprising the pharmaceutical composition of the above-mentioned (15), and a written matter associated therewith, the written matter stating that the pharmaceutical composition can or should be used for the prophylaxis or treatment of diabetic nephropathy.

BEST MODE FOR EMBODYING THE INVENTION

In the present invention, "AGEs" refers to compounds formed by non-enzymatic reaction of sugar with amino group of protein to create Schiff base and then Amadori compound, of which pentosidine, carboxymethyllysin, pyrraline and the like have been identified.

In the present invention, the "C1-6 alkyl group" is a linear or branched chain alkyl group having 1 to 6 carbon atoms and, for example, methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl and 1,2,2-trimethylpropyl can be mentioned. For $R^{1A}$, a propyl group is preferable. For $R^{2A}$ and $R^{3A}$, a C1-3 alkyl group is preferable. For $R^{4A}$, a C1-3 alkyl group is preferable, and an ethyl group and a propyl group are more preferable. For $R^{5A}$ and $R^{6A}$, a C1-3 alkyl group is preferable, and a methyl group is more preferable.

The "C6-10 arylene group" is a divalent aromatic C6-10 hydrocarbon group and, for example, a phenylene group, an indenylene group and a naphthylene group can be mentioned. For Y, a phenylene group is preferable.

The "C1-10 alkyl carbonyl group" is a group wherein a linear or branched chain C1-10 alkyl group is bonded to a carbonyl group and, for example, an alkylcarbonyl group such as acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl and undecanoyl can be mentioned. For $R^{7A}$, a C4-7 alkyl carbonyl group is preferable, and an octanoyl group is more preferable.

In the present invention, A is preferably a group represented by (A1) or (A3), more preferably a group represented by (A3).

In the present invention, B is preferably a 1H-tetrazol-5-yl group.

In the present invention, X is preferably methylene or an oxygen atom, more preferably methylene.

In the present invention, Y is preferably a single bond or phenylene, more preferably phenylene.

In the present invention, $R^{1A}$ is preferably a propyl group or a hydrogen atom, more preferably a propyl group.

In the present invention, $R^{2A}$ and $R^{3A}$ are the same or different and each is preferably a hydrogen atom, a carboxyl group or a pharmacologically acceptable ester thereof.

In the present invention, $R^{4A}$ is preferably an ethyl group or a propyl group.

In the present invention, $R^{5A}$ and $R^{6A}$ are each preferably a methyl group or a hydrogen atom.

In the present invention, $R^{7A}$ is preferably a C4-7 alkyl carbonyl group, more preferably an octanoyl group.

When the phenylene derivative represented by the above-mentioned formula (I) of the present invention has a basic group, it can be converted to an acid addition salt thereof according to a conventional method. As such a salt, for example salts with hydrohalic acids such as hydrofluoric acid, hydrochloric acid, hydrobromic acid, hydroiodic acid and the like; salts with inorganic acids such as nitrate, perchlorate, sulfate, phosphate and the like; salts with lower alkanesulfonic acids such as methanesulfonic acid, trifluoromethanesulfonic acid, ethanesulfonic acid and the like; salts with arylsulfonic acids such as benzenesulfonic acid, p-toluenesulfonic acid and the like; salts with amino acids such as glutamic acid, asparagine acid and the like; and salts with carboxylic acids such as acetic acid, fumaric acid, tartaric acid, oxalic acid, maleic acid, malic acid, succinic acid, benzoic acid, mandelic acid, ascorbic acid, lactic acid, gluconic acid, citric acid and the like, can be mentioned. It is preferably a salt with hydrohalic acid.

Moreover, when the phenylene derivative represented by the above-mentioned formula (I) has a carboxyl group, it can be converted to a metal salt thereof according to a conventional method. As such a salt, for example, salts of alkali metals such as lithium, sodium, potassium and the like; salts of alkaline earth metals such as calcium, barium, magnesium and the like; and aluminum salt can be mentioned. It is preferably an alkali metal salt.

The phenylene derivative represented by the above-mentioned formula (I) of the present invention can be converted to a pharmacologically acceptable ester thereof according to a conventional method. Such ester is not particularly limited as long as it is medically usable and pharmacologically acceptable.

As the ester residue of the ester of the phenylene derivative represented by the above-mentioned formula (I) of the present invention, for example, a linear or branched chain C1-6 alkyl group (the alkyl group is optionally substituted by a trialkylsilyl group), a C7-19 aralkyl group, a linear or branched chain C1-5 alkyl group substituted by linear or branched chain C1-6 alkanoyloxy, a linear or branched chain C1-5 alkyl group substituted by linear or branched chain C1-6 alkyloxycarbonyloxy, a linear or branched chain C1-5 alkyl group substituted by C5-7 cycloalkyl carbonyloxy, a linear or branched chain C1-5 alkyl group substituted by C5-7 cycloalkyloxycarbonyloxy, a linear or branched chain C1-5 alkyl group substituted by C6-10 aryl carbonyloxy, a linear or branched chain C1-5 alkyl group substituted by C6-10 aryloxycarbonyloxy, and a (2-oxo-1,3-dioxolen-4-yl)methyl group having linear or branched chain C1-6 alkyl as a substituent at the 5-position can be mentioned.

Here, as the linear or branched chain C1-6 alkyl group, for example, methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl and 1,2,2-trimethylpropyl can be mentioned, and it is preferably a linear or branched chain C1-4 alkyl group, more preferably methyl, ethyl, propyl, isopropyl, butyl or isobutyl, most preferably methyl or ethyl.

As the C7-19 aralkyl group, for example, benzyl, phenethyl, 3-phenylpropyl, 4-phenylbutyl, 1-naphthylmethyl, 2-naphthylmethyl and diphenylmethyl can be mentioned, and it is preferably benzyl.

As the C5-7 cycloalkyl group, for example, cyclopentyl, cyclohexyl and cycloheptyl, can be mentioned, and it is preferably cyclohexyl.

As the C6-10 aryl group, for example, phenyl and naphthyl can be mentioned, and it is preferably phenyl.

Specific preferably examples of the ester residue include methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy) ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy) ethyl, butoxycarbonyloxymethyl, 1-(butoxycarbonyloxy) ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl, cyclohexanecarbonyloxymethyl, 1-(cyclohexanecarbonyloxy)ethyl, cyclopentyloxycarbonyloxymethyl, 1-(cyclopentyloxycarbonyloxy) ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl, (5-methyl-2-oxo-1,3-dioxolen-4-yl)methyl, 2-trimethylsilylethyl and phthalidyl, more preferably (5-methyl-2-oxo-1,3-dioxolen-4-yl)methyl, pivaloyloxymethyl and 1-(isopropoxycarbonyloxy)ethyl.

When the phenylene derivative represented by the above-mentioned formula (I), a salt thereof or an ester thereof forms a solvate (e.g., hydrate), the present invention also encompasses such solvate.

Moreover, the present invention also encompasses a compound (e.g., prodrug such as amide derivative) that converts to the phenylene derivative represented by the above-mentioned formula (I), a salt thereof or an ester thereof by metabolism in living organisms.

Specific examples of the phenylene derivative represented by the above-mentioned formula (I) or a pharmacologically acceptable salt thereof or an ester thereof of the present invention include the compounds shown as examples below. However, the present invention is not limited to the following example compounds.

In the following Tables 1 to 3, "Me" shows a methyl group, "Et" shows an ethyl group, "Pr" shows a propyl group, "Bu" shows a butyl group, "t-Bu" shows a t-butyl group, "Hex" shows a hexyl group, "-Ph-" shows a phenylene group, "DMDO" shows a (5-methyl-2-oxo-1,3-dioxolen-4-yl)methyl group, "PHT" shows a phthalidyl group, "Tez" shows a 1H-tetrazol-5-yl group, "Tzd" shows a 2,4-dioxothiazolidin-5-yl group, and "—" shows a single bond.

TABLE 1

| No. | B | X | Y | $R^{1A}$ | $R^{2A}$ | $R^{3A}$ |
|---|---|---|---|---|---|---|
| 1-1 | 2'-Tez | $CH_2$ | -Ph- | Pr | H | 7-COOH |
| 1-2 | 2'-Tez | $CH_2$ | -Ph- | Pr | H | 7-COO-Me |
| 1-3 | 2'-Tez | $CH_2$ | -Ph- | Pr | H | 7-COO-Et |
| 1-4 | 2'-Tez | $CH_2$ | -Ph- | Pr | H | 7-COO-Pr |
| 1-5 | 2'-Tez | $CH_2$ | -Ph- | Pr | H | 7-COO-Bu |
| 1-6 | 2'-Tez | $CH_2$ | -Ph- | Pr | H | 7-COO-$^t$-Bu |
| 1-7 | 2'-Tez | $CH_2$ | -Ph- | Pr | H | 7-COO-Hex |
| 1-8 | 2'-Tez | $CH_2$ | -Ph- | Pr | H | 7-COO-DMDO |
| 1-9 | 2'-Tez | $CH_2$ | -Ph- | Pr | H | 7-COO-PHT |
| 1-10 | 2'-Tez | $CH_2$ | -Ph- | Pr | H | 6-COOH |
| 1-11 | 4'-Tez | $CH_2$ | — | Pr | H | 7-COOH |
| 1-12 | 2'-Tez | $CH_2$ | -Ph- | H | H | 7-COOH |
| 1-13 | 2'-Tez | $CH_2$ | -Ph- | Me | H | 7-COOH |
| 1-14 | 2'-Tez | $CH_2$ | -Ph- | Et | H | 7-COOH |
| 1-15 | 2'-Tez | $CH_2$ | -Ph- | Bu | H | 7-COOH |
| 1-16 | 2'-Tez | $CH_2$ | -Ph- | Pen | H | 7-COOH |
| 1-17 | 2'-Tez | $CH_2$ | -Ph- | Hex | H | 7-COOH |
| 1-18 | 2'-Tez | $CH_2$ | -Ph- | Pr | 6-Me | 7-COOH |
| 1-19 | 4'-Tez | O | — | Pr | H | 6-COOH |
| 1-20 | 2'-Tez | O | -Ph- | Pr | H | 6-COOH |
| 1-21 | 2'-Tez | O | -Ph- | Pr | H | 6-COO-Me |
| 1-22 | 2'-Tez | O | -Ph- | Pr | H | 6-COO-DMDO |
| 1-23 | 4'-Tez | O | — | Pr | H | 6-COOH |
| 1-24 | 2'-Tez | O | -Ph- | Bu | H | 6-COOH |
| 1-25 | 2'-Tez | S | -Ph- | Pr | H | 6-COOH |
| 1-26 | 2'-Tez | S | -Ph- | Pr | H | 6-COO-Me |
| 1-27 | 2'-Tez | S | -Ph- | Pr | H | 6-COO-DMDO |
| 1-28 | 2'-Tzd | $CH_2$ | -Ph- | Pr | H | 7-COOH |
| 1-29 | 2'-Tez | $CH_2$ | -Ph- | H | H | H |
| 1-30 | 4'-Tez | S | -Ph- | Pr | H | 6-COOH |
| 1-31 | 4'-Tzd | $CH_2$ | -Ph- | Pr | H | 7-COOH |
| 1-32 | 4'-Tzd | $CH_2$ | -Ph- | Pr | H | 7-COO-Et |

TABLE 2

| No. | B | Y | $R^{4A}$ | $R^{5A}$ | $R^{6A}$ |
|---|---|---|---|---|---|
| 2-1 | 4'-Tzd | — | Me | 7-Me | 5-Me |
| 2-2 | 4'-Tzd | — | Et | 7-Me | 5-Me |
| 2-3 | 2'-Tzd | -Ph- | Et | 7-Me | 5-Me |
| 2-4 | 4'-Tzd | — | Et | H | 5-Me |
| 2-5 | 4'-Tzd | — | Et | 7-Me | H |
| 2-6 | 4'-Tzd | — | Et | H | H |

TABLE 2-continued

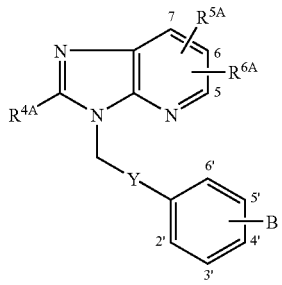

| No. | B | Y | $R^{4A}$ | $R^{5A}$ | $R^{6A}$ |
|---|---|---|---|---|---|
| 2-7 | 4'-Tzd | — | Et | 7-Me | 5-Et |
| 2-8 | 4'-Tzd | — | Et | 7-Me | 6-Me |
| 2-9 | 4'-Tzd | — | Et | 7-Me | 5-Pr |
| 2-10 | 4'-Tzd | — | Et | 7-Me | 5-Bu |
| 2-11 | 4'-Tzd | — | Et | 7-Me | 5-Hex |
| 2-12 | 4'-Tzd | — | Pr | 7-Me | 5-Me |
| 2-13 | 2'-Tzd | -Ph- | Pr | 7-Me | 5-Me |
| 2-14 | 4'-Tzd | — | Pr | H | 5-Me |
| 2-15 | 4'-Tzd | — | Bu | 7-Me | 5-Me |
| 2-16 | 4'-Tzd | — | Pn | 7-Me | 5-Me |
| 2-17 | 4'-Tzd | — | Hex | 7-Me | 5-Me |
| 2-18 | 4'-Tzd | — | Et | 7-Me | 5-Me |

TABLE 3

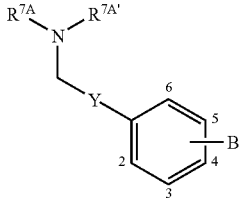

| No. | B | Y | $R^{7A}$ | $R^{7A'}$ |
|---|---|---|---|---|
| 3-1 | 4-Tez | — | $CH_3-(CH_2)_3-CO-$ | (3-COOH)-Ph |
| 3-2 | 4-Tez | — | $CH_3-(CH_2)_3-CO-$ | (3-COO-DMDO)-Ph |
| 3-3 | 2-Tez | -Ph- | $CH_3-(CH_2)_2-CO-$ | (3-COOH)-Ph |
| 3-4 | 2-Tez | -Ph- | $CH_3-CO-$ | (3-COOH)-Ph |
| 3-5 | 2-Tez | -Ph- | $CH_3-CH_2-CO-$ | (3-COOH)-Ph |
| 3-6 | 2-Tez | -Ph- | $CH_3-(CH_2)_2-CO-$ | (3-COOH)-Ph |
| 3-7 | 2-Tez | -Ph- | $CH_3-(CH_2)_3-CO-$ | (3-COOH)-Ph |
| 3-8 | 2-Tez | -Ph- | $CH_3-(CH_2)_3-CO-$ | (2-COOH)-Ph |
| 3-9 | 2-Tez | -Ph- | $CH_3-(CH_2)_3-CO-$ | (3-COOH)-Ph |
| 3-10 | 2-Tez | -Ph- | $CH_3-(CH_2)_3-CO-$ | (4-COOH)-Ph |
| 3-11 | 2-Tez | -Ph- | $CH_3-(CH_2)_4-CO-$ | (3-COOH)-Ph |
| 3-12 | 2-Tez | -Ph- | $CH_3-(CH_2)_5-CO-$ | (3-COOH)-Ph |
| 3-13 | 2-Tez | -Ph- | $CH_3-(CH_2)_6-CO-$ | (3-COOH)-Ph |
| 3-14 | 2-Tez | -Ph- | $CH_3-(CH_2)_8-CO-$ | (3-COOH)-Ph |
| 3-15 | 2-Tez | -Ph- | $CH_3-(CH_2)_9-CO-$ | (3-COOH)-Ph |
| 3-16 | 2-Tzd | -Ph- | $CH_3-(CH_2)_6-CO-$ | (3-COOH)-Ph |
| 3-17 | 2-Tez | -Ph- | $CH_3-(CH_2)_6-CO-$ | (2-COOH)-Ph |
| 3-18 | 4-Tez | -Ph- | $CH_3-(CH_2)_6-CO-$ | (3-COOH)-Ph |
| 3-19 | 2-Tez | -Ph- | $CH_3-(CH_2)_6-CO-$ | (4-COOH)-Ph |
| 3-20 | 2-Tez | -Ph- | $CH_3-(CH_2)_3-CO-$ | (3-COO-Me)-Ph |
| 3-21 | 2-Tez | -Ph- | $CH_3-(CH_2)_3-CO-$ | (3-COO-Et)-Ph |
| 3-22 | 2-Tez | -Ph- | $CH_3-(CH_2)_3-CO-$ | (3-COO-Pr)-Ph |
| 3-23 | 2-Tez | -Ph- | $CH_3-(CH_2)_3-CO-$ | (3-COO-Bu)-Ph |
| 3-24 | 2-Tez | -Ph- | $CH_3-(CH_2)_3-CO-$ | (3-COO-Hex)-Ph |
| 3-25 | 2-Tez | -Ph- | $CH_3-(CH_2)_3-CO-$ | (3-COO-DMDO)-Ph |
| 3-26 | 2-Tez | -Ph- | $CH_3-(CH_2)_6-CO-$ | (3-COO-DMDO)-Ph |
| 3-27 | 2-Tzd | -Ph- | $CH_3-(CH_2)_3-CO-$ | (3-COO-DMDO)-Ph |
| 3-28 | 2-Tez | -Ph- | $CH_3-(CH_2)_3-CO-$ | (3-COO-PHT)-Ph |
| 3-29 | 2-Tez | -Ph- | $CH_3-(CH_2)_7-CO-$ | (3-COOH)-Ph |
| 3-30 | 4-Tzd | — | $CH_3-(CH_2)_3-CO-$ | (3-COOH)-Ph |
| 3-31 | 4-Tzd | — | $CH_3-(CH_2)_3-CO-$ | (3-COO-Et)-Ph |
| 3-32 | 4-Tzd | — | $CH_3-(CH_2)_3-CO-$ | (3-COO-DMDO)-Ph |

In the above-mentioned Tables, preferable compounds are 1-1, 1-8, 1-10, 1-19, 1-20, 1-25, 1-29, 1-30, 2-2, 2-3, 2-12, 2-18, 3-3, 3-4, 3-5, 3-6, 3-7, 3-8, 3-9, 3-10, 3-13, 3-25, 3-29 and 3-30, and more preferable compounds are 1-1, 2-2, 3-7, 3-6, 3-3, 3-9, 3-13, 3-25 and 3-30.

The phenylene derivative represented by the above-mentioned formula (I), a pharmacologically acceptable salt thereof and a pharmacologically acceptable ester thereof of the present invention are useful as agents for the prophylaxis or treatment (particularly an agent for the treatment) of diabetic complications (particularly nephropathy).

The phenylene derivative represented by the above-mentioned formula (I), a pharmacologically acceptable salt thereof and a pharmacologically acceptable ester thereof of the present invention are administered in various forms. The form of administration is not particularly limited and determined depending on various dosage forms, age, sex and other conditions of patients, level of disease and the like. For example, tablet, pill, powder, granule, syrup, liquid, suspending agent, emulsion, granule and capsule are orally administered. In the case of injection, it is intravenously administered alone or in admixture with a normal supplemental liquid such as glucose, amino acid and the like and, where necessary, intramuscularly, intradermally, subcutaneously or intraperitoneally administered as it is. In the case of suppository, it is rectally administered. Preferably, it is orally administered.

These various preparations can be formed using a main drug and additives generally used in the field of drug products, such as excipient, binder, disintegrant, lubricant, solvent, flavoring agent, coating agent and the like, according to a conventional method For forming tablet, those conventionally known as a carrier in this field can be used. For example, excipients such as lactose, sucrose, sodium chloride, glucose, urea, starch, calcium carbonate, kaolin, crystalline cellulose, silicic acid and the like, binders such as water, ethanol, propanol, glucose solution, starch solution, gelatin solution, carboxymethylcellulose, shellac, methylcellulose, potassium phosphate, polyvinylpyrrolidone and the like, disintegrants such as dried starch, sodium alginate, agar powder, laminaran powder, sodium hydrogencarbonate, calcium carbonate, sorbitan polyoxyethylene fatty acid esters, sodium lauryl sulfate, stearic acid monoglyceride, starch, lactose and the like, disintegration inhibitors such as sucrose, stearic acid, cacao butter, hydrogenated oil and the like, absorption promoters such as quaternary ammonium bases, sodium lauryl sulfate and the like, humectants such as glycerol, starch and the like, adsorbents such as starch, lactose, kaolin, bentonite, colloidal silica and the like, lubricants such as purified talc, stearate, boric acid powder, polyethylene glycol and the like, and the like can be mentioned. Moreover, tablet can be formed into tablet having a conventional film, which includes sugar-coated tablet, gelatin-coated tablet, enteric-coated tablet, film-coated tablet, two-layered tablet and multi-layered tablet.

For forming pill, those conventionally known as carriers in this field can be widely used. For example, excipients such as glucose, lactose, starch, cacao butter, hydrogenated vegetable oil, kaolin, talc and the like, binders such as gum arabic powder, tragacanth powder, gelatin, ethanol and the like, disintegrants such as laminaran, agar and the like, and the like can be mentioned.

For forming suppository, those conventionally known as carriers in this field can be widely used. For example, polyethylene glycol, cacao butter, higher alcohol, higher alcohol esters, gelatin, semisynthesized glyceride and the like can be mentioned.

For forming injection, liquid and suspending agent to be used are preferably sterilized and isotonic with blood. For forming liquid, emulsion and suspending agent, those conventionally known as diluents in this field can be used. As the diluent, for example, water, ethyl alcohol, propylene glycol, isostearyl alcohol ethoxylate, polyoxy-isostearyl alcohol, sorbitan polyoxyethylene fatty acid esters and the like can be mentioned. In this case, sodium chloride, glucose or glycerol in an amount sufficient to prepare an isotonic solution may be added to a drug product, and conventional dissolution aids, buffer, soothing agent and the like may be added.

Where necessary, coloring agent, preservative, aroma, flavoring, sweetening agent and the like and other medicaments may be contained.

The amount of the above-mentioned compound, which is an active ingredient in the above-mentioned drug products, is not particularly limited and appropriately selected from a wide range. Generally, it is appropriately contained in a proportion of 1 to 70 wt %, preferably 1 to 30 mass %, of the entire composition.

While the dose thereof varies depending on the symptom, age, body weight, administration method, dosage form and the like, the lower limit for an adult is generally 0.01 mg (preferably 0.1 mg, more preferably 1 mg) and the upper limit is generally 2,000 mg (preferably 1,000 mg, more preferably 200 mg) per day, which is administered at once or in several portions.

The phenylene derivative represented by the following formula (I), a pharmacologically acceptable salt thereof and a pharmacologically acceptable ester thereof of the present invention can be produced, for example, by the following methods from a known compound as a starting material.

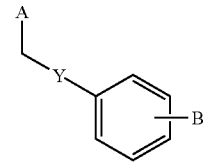

In the above-mentioned formula and in the following description, A, B, X, Y, $R^{1A}$, $R^{2A}$, $R^{3A}$, $R^{4A}$, $R^{5A}$, $R^{6A}$ and $R^{7A}$ are as defined above.

Step A

Method Aa

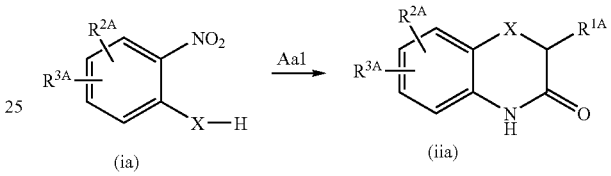

Method Ab

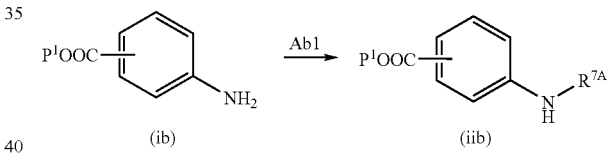

Method Ac

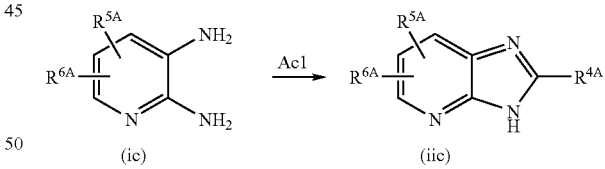

Step B

Method Ba

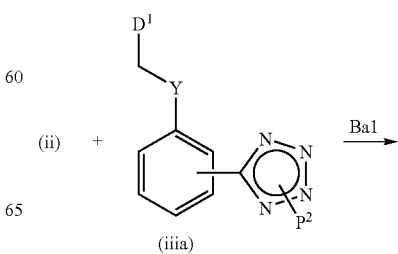

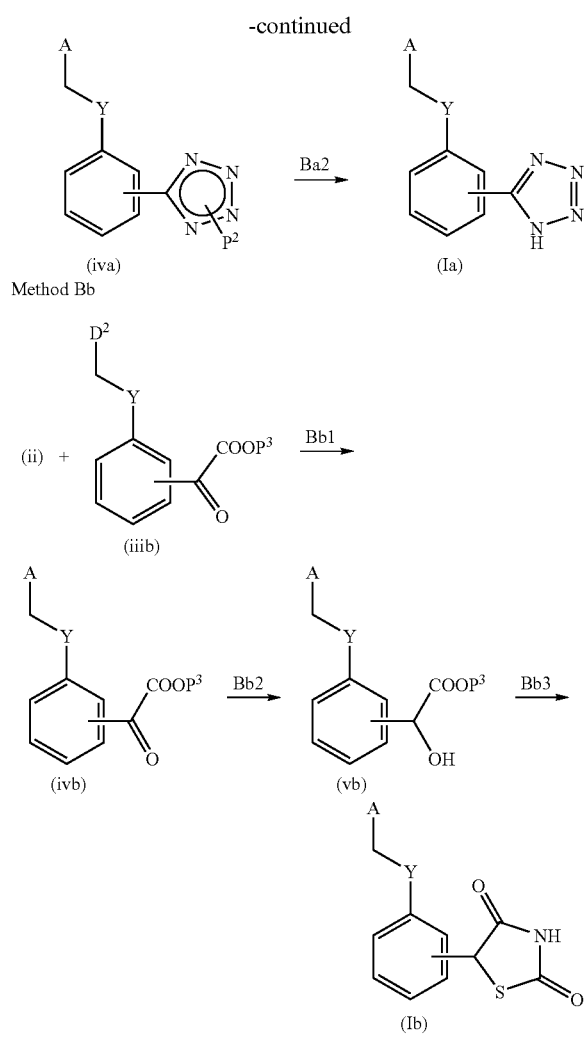

Method Bb

In the above-mentioned steps and in the following description, $P^1$ and $P^3$ are the same or different and each is a C1-6 alkyl group, $P^2$ is an amino-protecting group such as a trityl group, and $D^1$ and $D^2$ are the same or different and each is a leaving group such as a halogen atom and a sulfonyloxy group.

The production steps of compound (I) of the present invention consist of the following two steps.

That is,
(1) Step A is a step to produce heterocycle intermediate (ii) of compound (I), and Method Aa, Method Ab or Method Ac can be selected depending on the desired compound (iia), (iib) or (iic).
(2) Step B is a step to produce compound (I) of the present invention by condensing heterocycle intermediate (ii) obtained in Step A and phenylene intermediate (iii), and Method Ba or Method Bb can be selected depending on the desired compound (Ia) or (Ib).

Each step is explained in the following.

(Step A)

(Method Aa)

(Step Aa1)

In this step, compound (iia) is produced from known compound (ia). When X is methylene, the reaction and work-up according to the method described in Eur. J. Med. Chem. vol. 18(2), pp. 107-112 (1983) are performed to give compound (iia). When X is an oxygen atom, the reaction and work-up according to the method described in Chem. Pharm. Bull., vol. 46(11), pp. 1716-1723 (1998) are performed to give compound (iia). When X is a sulfur atom, the reaction and work-up according to the methods described in Can. J. Chem., vol. 43, pp. 2610-2612 (1965) and Chem. Pharm. Bull., vol 46(11), pp. 1716-1723 (1998) are performed to give compound (iia).

(Method Ab)

(Step Ab1)

In this step, compound (iib) is produced by introducing an alkylcarbonyl group into an amino group of known compound (ib). For this end, known compound (ib) is reacted with known alkanoic acid halide in an inert solvent.

The solvent to be used in the reaction is not particularly limited as long as it does not inhibit the reaction and dissolves the starting materials. For example, halogenated hydrocarbons such as dichloromethane, 1,2-dichloroethane, chloroform and the like; ethers such as diethyl ether, tetrahydrofuran, dioxane and the like; amides such as N,N-dimethylformamide, N,N-dimethylacetamide, hexamethylphosporic triamide and the like; esters such as ethyl formate, ethyl acetate and the like; sulfoxides such as dimethyl sulfoxide and the like; and a mixed solvent thereof can be mentioned, with preference given to N,N-dimethylacetamide and dimethyl sulfoxide.

For reaction of the acid halide and compound (ib), organic bases such as triethylamine and pyridine can be added as necessary. The reaction temperature is 0° C. to 100° C., preferably room temperature to 60° C. The reaction time is 10 min to 24 hrs, preferably 1 hr to 2 hrs.

(Method Ac)

(Step Ac1)

In this step, compound (iic) is produced from known compound (ic) and, for example, the reaction and work-up according to the method described in J. Med. Chem., vol. 34, pp. 2919-2922 (1991) are performed to give compound (iic).

(Step B)

(Method Ba)

(Step Ba1)

In this step, compound (iva) is produced from compound (ii) produced in Step A. For this end, compound (ii) is treated with known compound (iiia) in an inert solvent in the presence of a base.

The solvent to be used is not particularly limited as long as it does not inhibit the reaction and dissolves the starting materials. For example, ethers such as diethyl ether, tetrahydrofuran, dioxane and the like; amides such as N,N-dimethylformamide, N,N-dimethylacetamide, hexamethylphosporic triamide and the like; esters such as ethyl formate, ethyl acetate and the like; sulfoxides such as dimethyl sulfoxide and the like; and a mixed solvent thereof can be mentioned, with preference given to dioxane, N,N-dimethylacetamide and a mixed solvent thereof.

The base to be used is not particularly limited as long as it is used as a base for general reactions. Preferably, alkali metal hydrides such as lithium hydride, sodium hydride, .potassium hydride and the like; and alkali metal alkoxides such as sodium methoxide, sodium ethoxide, potassium methoxide, potassium ethoxide, potassium t-butoxide, lithium methoxide and the like, can be mentioned, with preference given to sodium hydride and potassium t-butoxide.

The reaction temperature is 0° C. to 100° C., preferably room temperature to 60° C. The reaction time is 10 min to 2 hrs, preferably 1 hr.

(Step Ba2)

In this step, the object compound (Ia) is produced from compound (iva). For this end, the protecting group of the tetrazole ring of compound (iva) is eliminated by a conventional method.

The deprotection is carried out by a known method and, for example, it can also be carried out according to Green and Wuts, "Protective group's in organic synthesis, 3rd Edition", Wiley-Interscience, USA.

(Method Bb)

(Step Bb1)

In this step, compound (ivb) is produced from compound (ii) produced in Step A and compound (iiib) under the same conditions as in Step Ba1.

Compound (ivb) is also produced by introducing an alkylcarbonyl group into an amino group when treating compound (ib) and compound (iiib) in the same manner as in Step Ba1.

(Step Bb2)

In this step, alcohol compound (vb) is produced. For this end, the carbonyl group in compound (ivb) is reduced with a reducing agent in a solvent.

The reducing agent to be used is not particularly limited as long as it is generally used for reducing a carbonyl group to an alcohol group. For example, alkali metal borohydrides such as sodium borohydride, lithium borohydride and the like can be mentioned, with preference given to sodium borohydride.

The solvent to be used is not particularly limited as long as it does not inhibit the reaction and dissolves the starting material to a certain extent. For example, alcohols such as methanol, ethanol and the like; ethers such as dioxane, ether, tetrahydrofuran and, the like; water and a mixed solvent of the above-mentioned solvent can be mentioned, with preference given to methanol and a mixed solvent of water and tetrahydrofuran.

The reaction temperature is −78° C. to 10° C., preferably −10° C. to 0° C. The reaction time is 10 min to 10 hrs, preferably 1 hr to 5 hrs.

(Step Bb3)

In this step, object compound (Ib) is produced. For this end, a leaving group is introduced into the hydroxyl group in compound (vb), the resulting compound is heated with thiourea in an inert solvent to achieve cyclization to give a 2-imino-4-oxothiazolidine ring, which is then treated with an acid.

When the leaving group is a halogen atom, the solvent to be used is not particularly limited as long as it does not inhibit the reaction and dissolves the starting material. For example, ethers such as diethyl ether, tetrahydrofuran, dioxane and the like; amides such as N,N-dimethylformamide, N,N-dimethylacetamide, hexamethylphosporic triamide and the like; halogenated hydrocarbons such as dichloromethane, chloroform, 1,2-dichloroethane and the like; nitriles such as acetonitrile, propionitrile and the like; esters such as ethyl formate, ethyl acetate and the like; and a mixed solvent thereof are preferable, halogenated hydrocarbons and ethers are more preferable, and dichloromethane and tetrahydrofuran are particularly preferable.

The halogenating agent to be used is not particularly limited as long as it is generally used for a reaction to convert a hydroxyl group to a halogen atom. For example, thionyl halides such as thionyl chloride, thionyl bromide, thionyl iodide and the like; sulfuryl halides such as sulfuryl chloride, sulfuryl bromide, sulfuryl iodide and the like; phosphorus trihalides such as phosphorus trichloride, phosphorus tribromide, phosphorus triiodide and the like; phosphorus pentahalides such as phosphorus pentachloride, phosphorus pentabromide, phosphorus pentaiodide and the like; and phosphorus oxyhalides such as phosphorus oxychloride, phosphorus oxybromide, phosphorus oxyiodide and the like can be mentioned.

The reaction temperature is 0° C. to under heating (boiling point of solvent to be used), preferably room temperature to under heating (boiling point of solvent to be used).

The reaction time is 10 min to 24 hrs, preferably 1 hr to 5 hrs.

When the leaving group is a sulfonyloxy group, the sulfonylating agent to be used is not particularly limited as long as it is generally used for sulfonylating a hydroxyl group. For example, alkanesulfonyl halides such as methanesulfonyl chloride and the like; arylsulfonyl halides such as p-toluenesulfonyl chloride and the like; and sulfonic anhydrides such as methanesulfonic anhydride, benzenesulfonic anhydride, trifluoromethanesulfonic anhydride and the like can be mentioned. Preferred are methanesulfonyl chloride, p-toluenesulfonyl chloride and trifluoromethanesulfonic anhydride.

The solvent to be used is not particularly limited as long as it does not inhibit the reaction and dissolves the starting material to a certain extent. For example, aliphatic hydrocarbons such as hexane, heptane, ligroin, petroleum ether and the like; aromatic hydrocarbons such as benzene, toluene, xylene and the like; halogenated hydrocarbons such as dichloromethane, chloroform, carbon tetrachloride, 1,2-dichloroethane, chlorobenzene, dichlorobenzene and the like; esters such as ethyl formate, ethyl acetate, propyl acetate, butyl acetate, diethyl carbonate and the like; and ethers such as diethyl ether, diisopropyl ether, tetrahydrofuran, dioxane, dimethoxyethane, diethyleneglycol dimethylether and the like can be mentioned. Preferred are halogenated hydrocarbons, esters and ethers, more preferred is dichloromethane.

The base to be used is not particularly limited as long as it is used as a base in general reactions. Preferred are organic bases such as triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU) and the like, with preference given to triethylamine.

The reaction temperature is 0° C. to 50° C., preferably 0° C. to room temperature. The reaction time is 10 min to 24 hrs, preferably 0.5 hr to 2 hrs.

The solvent to be used for heating cyclization reaction with thiourea is not particularly limited as long as it does not inhibit the reaction and dissolves the starting material to a certain extent. For example, alcohols such as methanol, ethanol and the like are preferable.

The reaction temperature is 50° C. to under heating (boiling point of solvent to be used), with preference given to the boiling point of the solvent to be used. The reaction time is 6 hrs to 48 hrs, preferably 12 hrs to 24 hrs.

By treating the 2-imino-4-oxothiazolidine ring in the cyclic compound thus obtained with an acid, the object compound (Ib) can be produced.

As the acid to be used, mineral acids such as hydrochloric acid, sulfuric acid and the like; and organic acids such as methanesulfonic acid, p-toluenesulfonic acid and the like can be mentioned, with preference given to hydrochloric acid. For this reaction, water; alcohols such as methanol, ethanol and the like; and ethers such as diethyl ether, dioxane and the like, can be mentioned, with preference given to water and alcohols. The reaction temperature is room temperature to 120° C., preferably 40° C. to 100° C. The reaction time is 1 hr to 24 hrs, preferably 2 hrs to 12 hrs.

After the completion of the reaction of each of the above-mentioned steps, the object compound is recovered from a reaction mixture according to a conventional method. For example, after a reaction mixture is appropriately neutralized or, when an insoluble material is present, after it is removed by filtration, an organic solvent immiscible with water, such as ethyl acetate, is added, the mixture is washed with water, an organic layer containing the object compound is separated and dried over anhydrous magnesium sulfate and the like, and the solvent is evaporated to give the object compound.

The obtained object product can be separated and purified as necessary by a conventional method, such as recrystallization and reprecipitation. Furthermore, it can be generally separated and purified by a method conventionally used for separation and purification of organic compounds, such as a method using a synthetic adsorbent such as adsorptive column chromatography, partition column chromatography and the like, a method using ion exchange chromatography, or elution with an appropriate eluent by an appropriately combination of normal phase and reversed-phase column chromatographys using silica gel or alkylated silica gel.

Moreover, when the above-mentioned compound (I) has a carboxyl group, a metal salt thereof can be produced according to a conventional method. When the above-mentioned compound (I) has a carboxyl group, a pharmacologically acceptable ester thereof can be produced according to a conventional method. Moreover, when the above-mentioned compound (I) has a carboxyl group, a prodrug such as a pharmacologically acceptable ester or amide thereof can be produced according to a conventional method.

EXAMPLES

The present invention is explained in detail by referring to Examples, Reference Examples, Experimental Example and Formulation Examples which are not to be construed as limitative.

Example 1

3-[N-[[4-[2-(1H-tetrazol-5-yl)phenyl]phenyl]methyl]-N-pentanoylamino]benzoic acid (Example Compound No. 3-9)

(1a) ethyl 3-[N-[[4-[2-(3-triphenylmethyl-3H-tetrazol-5-yl)phenyl]phenyl]methyl]-N-pentanoylamino]benzoate To a solution of ethyl 3-aminobenzoate (5.02 g) in N,N-dimethylacetamide (DMA, 50 ml) was added dropwise pentanoyl chloride (4.0 ml), and the mixture was stirred at room temperature for 1 hr. Saturated aqueous sodium hydrogencarbonate was added to the reaction mixture, and the mixture was stirred for 1 hr. The mixture was partitioned and extracted by adding ethyl acetate, and the extract was washed with saturated brine, dried over anhydrous sodium sulfate and concentrated to give ethyl 3-(N-pentanoyl)aminobenzoate (7.55 g).

To a solution of the obtained amide compound in DMA (100 ml) was added potassium tert-butoxide (4.09 g), and the mixture was stirred for 30 min. To the reaction mixture was added [4-[2-(3-triphenylmethyl-3H-tetrazol-5-yl)phenyl]phenyl]methylbromide (18.6 g), and the mixture was stirred at 50° C. for 3 hrs. The reaction mixture was added to ethyl acetate-water and, after partitioning and extraction, the extract was washed with saturated brine, dried over anhydrous sodium sulfate and concentrated. The residue was purified by silica gel column chromatography (eluted with hexane-ethyl acetate:3-2 v/v) to give the object compound (20.6 g, yield 93.6%).

$^1$H NMR (CDCl$_3$, 400 MHz): δ0.81 (3H, t, J=7.5Hz), 1.17-1.26 (2H, m), 1.38 (3H, t, J=7.0 Hz), 1.51-1.62 (2H, m), 2.02 (2H, t, J=7.5 Hz), 4.37 (2H, q, J=7.0 Hz), 4.81 (2H, bs), 6.91-6.96 (8H, m), 7.02 (2H, d, J=8.0 Hz), 7.21-7.26 (8H, m), 7.30-7.33 (3H, m), 7.37-7.50 (3H, m), 7.76 (1H, bs), 7.86-7.92 (2H, m).

(1b) 3-[N-[[4-[2-(1H-tetrazol-5-yl)phenyl]phenyl]methyl]-N-pentanoylamino]benzoic acid Ethyl 3-[N-[[4-[2-(3-triphenylmethyl-3H-tetrazol-5-yl)phenyl]phenyl]methyl]-N-pentanoylamino]benzoate (0.37 g) synthesized in Example 1a was dissolved in 75% acetic acid-water (8.8 ml), and the mixture was stirred at room temperature for 24 hrs. The reaction mixture was concentrated and dried to give a solid. The residue was dissolved in 75% dioxane-water (8.8 ml), lithium hydroxide (45 mg) was added, and the mixture was stirred at 50° C. for 24 hrs. The reaction mixture was concentrated to give a solid, and the residue was purified by silica gel column chromatography (methylene chloride-methanol:7-3 v/v) to give the object compound (0.12 g, yield 88%).

$^1$H NMR (DMSO-d$_6$, 400 MHz): δ0.75 (3H, t, J=7.5 Hz), 1.12-1.21 (2H, m), 2.05 (2H, bs), 4.86 (2H, s), 6.99 (2H, d, J=8.0 Hz), 7.10 (2H, d, J=8.0 Hz), 7.32 (1H, d, J=8.0 Hz), 7.46-7.56 (3H, m), 7.61-7.67 (2H, m), 7.71 (1H, bs), 7.85 (1H, d, J=7.5 Hz).

MS (FAB) M/z: 456 (M+H)$^+$.

Example 2

3-[N-[[4-[2-(1H-tetrazol-5-yl)phenyl]phenyl]methyl]-N-acetylamino]benzoic acid (Example Compound No. 3-4)

By the reaction and work-up according to Example 1, the object compound was obtained from ethyl 3-aminobenzoate, acetyl chloride and [4-[2-(3-triphenylmethyl-3H-tetrazol-5-yl)phenyl]phenyl]methylbromide.

$^1$H NMR (DMSO-d$_6$, 400 MHz): δ1.91 (3H, bs), 4.88 (2H, bs), 7.02 (2H, d, J=8.0 Hz), 7.15 (2H, d, J=8.0 Hz), 7.40 (1H, d, J=8.5 Hz), 7.49-7.55 (2H, m), 7.57 (1H, dd, J=1.0 and 7.5 Hz), 7.64-7.69 (2H, m).

MS (FAB) M/z: 414 (M+H)$^+$.

Example 3

3-[N-[[4-[2-(1H-tetrazol-5-yl)phenyl]phenyl]methyl]-N-propanoylamino]benzoic acid (Example Compound No. 3-5)

By the reaction and work-up according to Example 1, the object compound was obtained from ethyl 3-aminobenzoate, propionyl chloride and [4-[2-(3-triphenylmethyl-3H-tetrazol-5-yl)phenyl]phenyl]methylbromide.

¹H NMR (DMSO-d₆, 400 MHz): δ0.95 (3H, t, J=7.0 Hz), 2.08-2.1 (2H, m), 4.88 (2H, s), 7.01 (2H, d, J=8.5 Hz), 7.13 (2H, d, J=8.5 Hz), 7.37 (1H, d, J=7.5 Hz), 7.48-7.58 (3H, m), 7.64-7.69 (2H, m), 7.76 (1H, bs), 7.87 (1H, d, J=8.0 Hz).
MS (FAB) M/z: 428 (M+H)⁺.

Example 4

3-[N-[[4-[2-(1H-tetrazol-5-yl)phenyl]phenyl]methyl]-N-butanoylamino]benzoic acid (Example Compound No. 3-6)

By the reaction and work-up according to Example 1, the object compound was obtained from ethyl 3-aminobenzoate, butyryl chloride and [4-[2-(3-triphenylmethyl-3H-tetrazol-5-yl)phenyl]phenyl]methylbromide.
¹H NMR (DMSO-d₆, 400 MHz): δ0.78 (3H, t, J=7.0 Hz), 1.50 (2H, m), 2.00-2.08 (2H, m), 4.88 (2H, s), 7.01 (2H, d, J=8.0 Hz), 7.13 (2H, d, J=8.0 Hz), 7.35 (1H, d, J=8.0 Hz), 7.49-7.58 (3H, m), 7.64-7.69 (2H, m), 7.74 (1H, bs), 7.88 (1H, d, J=8.0 Hz).
MS (FAB) M/z: 442 (M+H)⁺.

Example 5

3-[N-[[4-[2-(1H-tetrazol-5-yl)phenyl]phenyl]methyl]-N-octanoylamino]benzoic acid (Example Compound No. 3-13)

By the reaction and work-up according to Example 1, the object compound was obtained from ethyl 3-aminobenzoate, octanoyl chloride and [4-[2-(3-triphenylmethyl-3H-tetrazol-5-yl)phenyl]phenyl]methylbromide.
¹H NMR (DMSO-d₆, 400 MHz): δ0.81 (3H, t, J=7.0 Hz), 1.10-1.24 (8H, m), 1.43-1.51 (2H, m), 2.01-2.09 (2H, m), 7.01 (2H, d, J=8.0 Hz), 7.12 (2H, d, J=8.0 Hz), 7.35 (1H, d, J=8.0 Hz), 7.48-7.61 (3H, m), 7.64-7.69 (2H, m), 7.74 (1H, bs), 7.88 (1H, d, J=8.0 Hz).
MS (FAB) M/z: 498 (M+H)⁺.

Example 6

(5-methyl-2-oxo-1,3-dioxolen-4-yl)methyl 3-[N-[[4-[2-(1H-tetrazol-5-yl)phenyl]phenyl]methyl]-N-pentanoylamino]benzoate (Example Compound No. 3-25)

To a solution of ethyl 3-[N-[[4-[2-(3-triphenylmethyl-3H-tetrazol-5-yl)phenyl]phenyl]methyl]-N-pentanoylamino]benzoate (11.50 g) synthesized in Example 1a in dioxane (100 ml) was added 1N-aqueous sodium hydroxide solution (19 ml), and the mixture was stirred at room temperature for 5 days. The reaction mixture was concentrated, ethyl acetate and saturated aqueous potassium bisulfate solution were added to carry out partitioning and extraction. The extracted organic layer was washed with saturated brine, dried over anhydrous sodium sulfate, filtrated and concentrated to give a crude product of 3-[N-[[4-[2-(3-triphenylmethyl-3H-tetrazol-5-yl)phenyl]phenyl]methyl]-N-pentanoylamino]benzoic acid. To a solution of the obtained crude product in DMA (90 ml) were added potassium carbonate (4.86 g) and a solution of 4-chloromethyl-5-methyl-1,3-dioxolen-2-one (3.92 g) in DMA (5 ml), and the mixture was stirred at room temperature for 24 hrs. The reaction mixture was poured into ethyl acetate-water to carry out partitioning and extraction. The extracted organic layer was washed with saturated brine, dried over anhydrous sodium sulfate, filtrated and concentrated, and the residue was purified by silica gel column chromatography (hexane-ethyl acetate:1-1 v/v) to give (5-methyl-2-oxo-1,3-dioxolen-4-yl)methyl3-[N-[[4-[2-(3-triphenylmethyl-3H-tetrazol-5-yl)phenyl]phenyl]methyl]-N-pentanoylamino] benzoate (11.57 g).

To a solution of the obtained (5-methyl-2-oxo-1,3-dioxolen-4-yl)methyl 3-[N-[[4-[2-(3-triphenylmethyl-3H-tetrazol-5-yl)phenyl]phenyl]methyl]-N-pentanoylamino]benzoate (11.57 g) in dioxane (80 ml) were added acetic acid (60 ml) and water (20 ml), and the mixture was stirred at 40° C. for 7 hrs. The reaction mixture was concentrated to give a solid, and the residue was purified by silica gel column chromatography (methylene chloride-methanol:10-1 v/v) to give the object compound (5.01 g).
¹H NMR (DMSO-d₆, 400 MHz): δ0.76 (3H, t, J=7.5 Hz), 1.11-1.22 (2H, m), 1.47 (2H, qt, J=7.5 Hz), 2.00-2.10 (2H, m), 2.21 (3H, s), 4.88 (2H, s), 5.22 (2H, s), 7.01 (2H, d, J=8.0 Hz), 7.12 (2H, d, J=8.0 Hz), 7.41 (1H, d, J=8.5 Hz), 7.51-7.58 (3H, m), 7.61-7.70 (2H, m), 7.78 (1H, bs), 7.91 (1H, d, J=7.5 Hz).
MS (FAB) M/z: 568 (M+H)⁺.

Example 7

3-[N-[[4-(1H-tetrazol-5-yl)phenyl]methyl]-N-pentanoylamino]benzoic acid (Example Compound No. 3-1)

By the reaction and work-up according to Example 1, the object compound was obtained from ethyl 3-aminobenzoate, pentanoyl chloride and [4-(3-triphenylmethyl-3H-tetrazol-5-yl)phenyl]methylbromide.
¹H NMR (DMSO-d₆, 400 MHz): δ0.77 (3H, t, J=7.5 Hz), 1.14-1.24 (2H, m), 1.49 (2H, qt, J=7.5 Hz), 2.04-2.34 (2H, m), 4.98 (2H, s), 7.43 (2H, d, J=8.0 Hz), 7.48-7.54 (2H, m), 7.72 (1H, m), 7.87 (1H, d, J=6.5 Hz), 7.96 (2H, d, J=8.0 Hz).
MS (FAB) M/z: 380 (M+H)⁺.

Example 8

2-[N-[[4-[2-(1H-tetrazol-5-yl)phenyl]phenyl]methyl]-N-pentanoylamino]benzoic acid (Example Compound No. 3-8)

By the reaction and work-up according to Example 1, the object compound was obtained from ethyl 2-aminobenzoate, pentanoyl chloride and [4-[2-(3-triphenylmethyl-3H-tetrazol-5-yl)phenyl]phenyl]methylbromide.
¹H NMR (DMSO-d₆, 400 MHz): δ0.74 (3H, t, J=7.5 Hz), 1.14 (2H, sex, J=7.5 Hz), 1.43 (2H, qt, J=7.5 Hz), 1.81-1.98 (2H, m), 3.89 (1H, d, J=15.0 Hz), 5.48 (1H, d, J=15.0 Hz), 6.82 (1H, dd, J=2.0 and 7.5 Hz), 6.97 (2H, d, J=8.0 Hz), 7.09 (2H, d, J=8.0 Hz), 7.45-7.55 (4H, m), 7.62-7.68 (2H, m), 7.91 (1H, dd, J=2.0 and 7.5 Hz).
MS (FAB) M/z: 456 (M+H)⁺.

Example 9

4-[N-[[4-[2-(1H-tetrazol-5-yl)phenyl]phenyl]methyl]-N-pentanoylamino]benzoic acid (Example Compound No. 3-10)

By the reaction and work-up according to Example 1, the object compound was obtained from ethyl 4-aminobenzoate, pentanoyl chloride and [4-[2-(3-triphenylmethyl-3H-tetrazol-5-yl)phenyl]phenyl]methylbromide.

¹H NMR (DMSO-d₆, 400 MHz): δ0.76 (3H, t, J=7.5 Hz), 1.17 (2H, sex, J=7.5 Hz), 1.46 (2H, qt J=7.5 Hz), 2.10 (2H, t, J=7.5 Hz), 4.87 (2H, s), 6.98 (2H, d, J=8.5 Hz), 7.09 (2H, d, J=8.5 Hz), 7.25 (2H, d, J=8.5 Hz), 7.49-7.56 (2H, m), 7.62-7.66 (2H, m), 7.91 (2H, d, J=8.5 Hz).

MS (FAB) M/z: 456 (M+H)⁺·.

Example 10

2-oxo-3-propyl-1-[[4-[2-(1H-tetrazol-5-yl)phenyl]phenyl]methyl]-1,3,4-trihydroquinoline-7-carboxylic acid (Example Compound No. 1-1)

(10a) methyl 2-oxo-3-propyl-1,3,4-trihydroquinoline-7-carboxylate

By the reaction and work-up according to the method described in Eur. J. Med. Chem., vol. 18(2), pp. 107-112 (1983), the object compound was obtained as white crystals (melting point: 122-124° C.) from 4-methyl-3-nitrobenzoic acid and diethyl n-propylmalonate.

¹H NMR (CDCl₃, 400 MHz): δ0.94 (3H, t, J=7.0 Hz), 1.35-1.53 (3H, m), 1.76-1.87 (1H, m), 2.54-2.61 (1H, m), 2.79 (1H, dd, J=8.5 and 16.0 Hz), 3.08 (1H, dd, J=6.0 and 16.0 Hz), 3.90 (3H, s), 7.22 (1H, t, J=7.5 Hz), 7.39 (1H, d, J=1.5 Hz), 7.64 (1H, dd, J=1.5 and 7.5 Hz), 7.82 (1H, bs).

MS (FAB) M/z: 248 (M+H)⁺·.

(10b) methyl 2-oxo-3-propyl-1-[[4-[2-(3-triphenylmethyl-3H-tetrazol-5-yl)phenyl]phenyl]methyl]-1,3,4-trihydroquinoline-7-carboxylate By the reaction and work-up according to Example 1a, the object compound was obtained as white crystals (melting point: 199-200° C. (dec.)) from methyl 2-oxo-3-propyl-1,3,4-trihydroquinoline-7-carboxylate synthesized in Example 10a.

¹H NMR (CDCl₃, 400 MHz): δ0.94 (3H, t, J=7.0 Hz), 1.41-1.56 (3H, m), 1.80-1.86 (1H, m), 2.68-2.71 (1H, m), 2.79 (1H, dd, J=8.0 and 15.5 Hz), 3.09 (1H, dd, J=5.0 and 15.0 Hz), 3.78 (3H, s), 5.10 (2H, dd, J=16.0 and 30.0 Hz), 6.92-6.94 (6H, m), 7.02-7.07 (4H, m), 7.21-7.28 (7H, m), 7.31-7.35 (4H, m), 7.40-7.48 (2H, m), 7.61 (1H, d, J=1.0 Hz), 7.65 (1H, dd, J=1.0 and 7.5 Hz), 7.88 (1H, dd, J=2.0 and 7.5 Hz).

MS (FAB) M/z: 762 (M+K)⁺·.

(10c) 2-oxo-3-propyl-1-[[4-[2-(1H-tetrazol-5-yl)phenyl]phenyl]methyl]-1,3,4-trihydroquinoline-7-carboxylic acid By the reaction and work-up according to Example 1b, the object compound was obtained from methyl 2-oxo-3-propyl-1-[[4-[2-(3-triphenylmethyl-3H-tetrazol-5-yl)phenyl]phenyl]methyl]-1,3,4-trihydroquinoline-7-carboxylate synthesized in Example 10b.

¹H NMR (DMSO-d₆, 400 MHz): δ0.89 (3H, t, J=7.0 Hz), 1.35-1.47 (3H, m), 1.67-1.73 (1H, m), 2.65-2.72 (1H, m), 2.83 (1H, dd, J=9.5 and 15.5 Hz), 3.15 (1H, dd, J=5.5 and 15.5 Hz), 5.15 (2H, s), 7.05 (2H, d, J=8.0 Hz), 7.14 (2H, d, J=8.0 Hz), 7.38 (1H, d, J=7.5 Hz), 7.43 (1H, d, J=1.0 Hz), 7.54-7.58 (3H, m), 7.63-7.68 (2H, m).

MS (FAB) M/z: 468 (M+H)⁺·.

Example 11

2-oxo-3-propyl-1-[[4-[2-(1H-tetrazol-5-yl)phenyl]phenyl]methyl]-1,3,4-trihydroquinoline-6-carboxylic acid (Example Compound No. 1-10)

(11a) methyl 2-oxo-3-propyl-1,3,4-trihydroquinoline-6-carboxylate

By the reaction and work-up according to the method described in Eur. J. Med. Chem., vol. 18(2), pp. 107-112 (1983), the object compound was obtained as white crystals (9.3 g, melting point: 200-202° C.) from 3-methyl-4-nitrobenzoic acid (25.0 g) and diethyl n-propylmalonate.

¹H NMR (CDCl₃, 400 MHz): δ(3H, t, J=7.0 Hz), 1.37-1.53 (3H, m), 1.75-1.85 (1H, m), 2.55-2.62 (1H, m), 2.79 (1H, dd, J=8.5 and 16.0 Hz), 3.09 (1H, dd, J=6.0 and 16.0 Hz), 3.89 (3H, s), 6.76 (1H, d, J=8.5 Hz), 7.84-7.86 (2H, m), 8.11 (1H, bs).

MS (EI) M/z: 247 (M)⁺·.

(11b) 2-oxo-3-propyl-1-[[4-[2-(1H-tetrazol-5-yl)phenyl]phenyl]methyl]-1,3,4-trihydroquinoline-6-carboxylic acid By the reaction and work-up according to Examples 10b and 10c, the object compound was obtained from methyl 2-oxo-3-propyl-1,3,4-trihydroquinoline-6-carboxylate synthesized in Example 11a.

¹H NMR (DMSO-d₆, 400 MHz): δ0.90 (3H, t, J=7.0 Hz), 1.32-1.48 (3H, m), 1.64-1.73 (1H, m), 2.66-2.73 (1H, m), 2.82 (1H, dd, J=9.5 and 15.5 Hz), 3.13 (1H, dd, J=6.0 and 15.5 Hz), 5.16 (2H, s), 6.98 (1H, d, J=9.0 Hz), 7.04 (2H, d, J=8.0 Hz), 7.13 (2H, d, J=8.0 Hz), 7.51-7.57 (2H, m), 7.64 (2H, d, J=8.5 Hz), 7.71 (1H, dd, J=2.0 and 8.5 Hz), 7.81 (1H, d, J=2.0 Hz).

MS (FAB) M/z: 468 (M+H)⁺·.

Example 12

(5-methyl-2-oxo-1,3-dioxolen-4-yl)methyl2-oxo-3-propyl-1-[[4-[2-(1H-tetrazol-5-yl)phenyl]phenyl]methyl]-1,3,4-trihydroquinoline-7-carboxylate (Example Compound No. 1-8)

By the reaction and work-up according to Example 6, the object compound was obtained from methyl 2-oxo-3-propyl-1-[[4-[2-(3-triphenylmethyl-3H-tetrazol-5-yl)phenyl]phenyl]methyl]-1,3,4-trihydroquinoline-7-carboxylate obtained in Example 10b.

¹H NMR (DMSO-d₆, 400 MHz): δ0.89 (3H, t, J=7.0 Hz), 1.33-1.47 (3H, m), 1.66-1.72 (1H, m), 2.17 (3H, s), 2.67-2.71 (1H, m), 2.85 (1H, dd, J=9.0 and 16.0 Hz), 3.16 (1H, dd, J=5.0 and 16.0 Hz), 3.57 (2H, s), 5.15 (2H, s), 7.05 (2H, d, J=8.0 Hz), 7.15 (2H, d, J=8.0 Hz), 7.41 (1H, d, J=8.0 Hz), 7.45 (1H, s).

MS (FAB) M/z: 580 (M+H)⁺, 602 (M+Na)⁺·.

Example 13

1-[[4-[2-(1H-tetrazol-5-yl)phenyl]phenyl]methyl]-1,3,4-trihydroquinolin-2-one (Example Compound No. 1-29)

By the reaction and work-up according to Examples 1a and 1b, the object compound was obtained from 1,3,4-trihydroquinolin-2-one (Aldrich).

¹H NMR (DMSO-d₆, 400 MHz): δ2.69 (2H, t, J=7.5 Hz), 2.95 (2H, t, J=7.5 Hz), 5.13 (2H, s); 6.89 (1H, d, J=8.0 Hz), 6.97 (1H, t, J=7.5 Hz), 7.03 (2H, d, J=8.0 Hz), 7.12 (1H, d, J=7.5 Hz), 7.16 (2H, d, J=8.0 Hz), 7.23 (1H, d, J=6.5 Hz), 7.52-7.57 (2H, m), 7.63-7.68 (2H, m).
MS (FAB) M/z: 382 (M+H)⁺·.

Example 14

3-oxo-2-propyl-4-[[4-[2-(1H-tetrazol-5-yl)phenyl]phenyl]methyl]-2H-benzo[e]1,4-oxazine-6-carboxylic acid (Example Compound No. 1-20)

(14a) methyl 3-oxo-2-propyl-2H,4H-benzo[e]1,4-oxazine-6-carboxylate

By the reaction and work-up according to the method described in Chem. Pharm. Bull., vol. 46(11), pp. 1716-1723 (1998), the object compound was obtained as white crystals (10.0 g, melting point: 149-150° C.) from methyl 4-hydroxy-3-nitrobenzoate (23.6 g) and ethyl 2-bromopentanoate.
¹H NMR (CDCl₃, 400 MHz): δ0.98 (3H, t, J=7.5 Hz), 1.48-1.65 (2H, m), 1.81-1.94 (2H, m), 3.89 (3H, s), 4.65 (1H, dd, J=4.5 and 8.0 Hz), 6.98 (1H, d, J=8.0 Hz), 7.48 (1H, d, J=2.0 Hz), 7.67 (1H, dd, J=2.0 and 8.0 Hz), 8.13 (1H, bs).
MS (FAB) M/z: 250 (M+H)⁺·.

(14b) 3-oxo-2-propyl-4-[[4-[2-(1H-tetrazol-5-yl)phenyl]phenyl]methyl]-2H-benzo[e]1,4-oxazine-6-carboxylic acid By the reaction and work-up according to Examples 1a and 1b, the object compound (melting point: 197-198° C.) was obtained from methyl 3-oxo-2-propyl-2H,4H-benzo[e]1,4-oxazine-6-carboxylate synthesized in Example 14a.
¹H NMR (DMSO-d₆, 400 MHz): δ0.94 (3H, t, J=7.5 Hz), 1.46-1.57 (2H, m), 1.79-1.88 (2H, m), 4.91 (1H, dd, J=5.0 and 8.0 Hz), 5.17 (2H, s), 7.08 (2H, d, J=8.0 Hz), 7.13 (1H, d, J=8.0 Hz), 7.19 (2H, d, J=8.0 Hz), 7.52-7.68 (6H, m).
MS (FAB) M/z: 470 (M+H)⁺·.

Example 15

3-oxo-2-propyl-4-[4-[4-(1H-tetrazol-5-yl)phenyl]methyl]2-H-benzo[e]1,4-oxazine-6-carboxylic acid (Example Compound No. 1-23)

By the reaction and work-up according to Examples 1a and 1b, the object compound (melting point: >260° C.) was obtained from methyl 3-oxo-2-propyl-2H,4H-benzo[e]1,4-oxazine-6-carboxylate synthesized in Example 14a and [4-(3-triphenylmethyl-3H-tetrazol-5-yl)phenyl]methylbromide.
¹H NMR (DMSO-d₆, 400 MHz): δ0.96 (3H, t, J=7.5 Hz), 1.48-1.59 (2H, m), 1.84-1.91 (2H, m), 4.96 (1H, dd, J=5.0 and 8.0 Hz), 5.28 (2H, dd, J=17.0 and 23.5 Hz), 7.14 (1H, d, J=8.0 Hz), 7.48 (1H, d, J=2.0 Hz), 7.49 (2H, d, J=8.5 Hz), 7.60 (1H, dd, J=2.0 and 8.0 Hz), 8.02 (2H, d, J=8.5 Hz).
MS (FAB) M/z: 394 (M+H)⁺·.

Example 16

3-oxo-2-propyl-4-[[4-[2-(1H-tetrazol-5-yl)phenyl]phenyl]methyl]-2H-benzo[e]1,4-thiazine-6-carboxylic acid (Example Compound No. 1-25)

(16a) methyl 3-oxo-2-propyl-2H,4H-benzo[e]1,4-thiazine-6-carboxylate

By the reaction and work-up according to the method described in Chem. Pharm. Bull., vol. 46(11), pp. 1716-1723 (1998), the object compound was obtained as white crystals (8.4 g) from 2-bromopentanoic acid and 3-amino-4-mercaptobenzoic acid obtained by the method described in Can. J. Chem., vol. 43, pp. 2610-2612 (1965) from 4-chloro-3-nitrobenzoic acid (50.0 g).
¹H NMR (CDCl₃, 400 MHz): δ0.93 (3H, t, J=7.0 Hz), 1.39-1.64 (3H, m), 1.85-1.93 (1H, m), 3.47 (1H, dd, J=6.0 and 8.5 Hz), 3.92 (3H, s), 7.38 (1H, d, J=8.5 Hz), 7.54 (1H, d, J=1.5 Hz), 7.68 (1H, dd, J=1.5 and 8.5 Hz), 8.50 (1H, bs).
MS (EI) M/z: 265 (M)⁺·.

(16b) 3-oxo-2-propyl-4-[[4-[2-(1H-tetrazol-5-yl)phenyl]phenyl]methyl]-2H-benzo[e]1,4-thiazine-6-carboxylic acid By the reaction and work-up according to Examples 1a and 1b, the object compound was obtained from methyl 3-oxo-2-propyl-2H,4H-benzo[e]1,4-thiazine-6-carboxylate synthesized in Example 16a.
¹H NMR (DMSO-d₆, 400 MHz): δ0.88 (3H, t, J=7.5 Hz), 1.23-1.56 (3H, m), 1.75-1.85 (1H, m), 3.81 (1H, t, J=7.0 Hz), 5.21 (2H, dd, J=14.0 and 41.0 Hz), 5.15-5.28 (2H, m), 7.05 (4H, bs), 7.37-7.41 (3H, m), 7.55-7.67 (4H, m).
MS (FAB) M/z: 486 (M+H)⁺·.

Example 17

3-oxo-2-propyl-4-[[4-(1H-tetrazol-5-yl)phenyl]methyl]2-H-benzo[e]1,4-thiazine-6-carboxylic acid (Example Compound No. 1-30)

By the reaction and work-up according to Examples 1a and 1b, the object compound was obtained from methyl 3-oxo-2-propyl-2H,4H-benzo[e]1,4-thiazine-6-carboxylate synthesized in Example 16a and [4-(3-triphenylmethyl-3H-tetrazol-5-yl)phenyl]methylbromide.
¹H NMR (DMSO-d₆, 400 MHz): δ0.90 (3H, t, J=7.5 Hz), 1.37-1.60 (3H, m), 1.82-1.89 (1H, m), 3.88 (1H, dd, J=6.0 and 8.5 Hz), 5.35 (2H, ABq, J=17.0 and 31.5 Hz), 7.41 (2H, d, J=8.5 Hz), 7.56-7.62 (3H, m), 8.01 (2H, d, J=8.5 Hz).
MS (FAB) M/z: 410 (M+H)⁺·.

Example 18

5-[4-[(2-ethyl-5,7-dimethylimidazo[4,5-b]pyridin-3-yl)methyl]phenyl]-1,3-thiazolidine-2,4-dione (Example Compound No. 2-18)

(18a) methyl 2-[4-[(2-ethyl-5,7-dimethylimidazo[4,5-b]pyridin-3-yl)methyl]phenyl]-2-oxoacetate To a solution of potassium tert-butoxide (23.6 g) in DMA (200 ml) was added dropwise a solution of 2-ethyl-5,7-dimethylimidazo[4,5-b]pyidine (33.5 g) in DMA (200 ml), and a solution of methyl 2-[4-(bromomethyl)phenyl]-2-oxoacetate (54.1 g) in DMA (100 ml) was added dropwise while maintaining the reaction mixture at not more than 10° C. The mixture was stirred at room temperature for 30 min, and the reaction mixture was added to ethyl acetate-water to carry out partitioning and extraction. The extracted organic layer was washed with saturated brine, dried over anhydrous sodium sulfate, filtrated and concentrated. The obtained residue was purified by silica gel column chromatography (hexane-ethyl acetate:2-1 v/v) to give the object compound (18.5 g).

(18b) methyl 2-[4-[(2-ethyl-5,7-dimethylimidazo[4, 5-b]pyridin-3-yl)methyl]phenyl]-2-hydroxyacetate To a suspension of methyl 2-[4-[(2-ethyl-5,7-dimethylimidazo[4,5-b]pyridin-3-yl)methyl]phenyl]-2-oxoacetate (21.5 g) obtained in 18a in methanol (215 ml) was added sodium borohydride (638 mg) by a small portion while maintaining the mixture at not more than 0° C. After confirmation of the disappearance of the starting material by thin layer chromatography, methanol was evaporated under reduced pressure, and the concentrate was dissolved in ethyl acetate-water to carry out partitioning and extraction. The extracted organic layer was washed with saturated brine, dried over anhydrous sodium sulfate, filtrated and concentrated. The obtained residue was purified by silica gel column chromatography (hexane-ethyl acetate:1-1 v/v) to give the object compound (23.4 g) in an amorphous form.

(18c) 5-[4-[(2-ethyl-5,7-dimethylimidazo[4,5-b]pyridin-3-yl)methyl]phenyl]thiazolidine-2,4-dione To a solution of methyl 2-[4-[(2-ethyl-5,7-dimethylimidazo[4,5-b]pyridin-3-yl)methyl]phenyl]-2-hydroxyacetate (6.82 g) obtained in 18b and triethylamine (3.2 ml) in dichloromethane (69 ml) was added dropwise a solution of methanesulfonyl chloride (1.8 ml) in dichloromethane (1 ml) at not more than 5° C. After stirring at not more than 5° C. for 30 min, dichloromethane was evaporated under reduced pressure, and the residue was dissolved in ethyl acetate-water to carry out partitioning and extraction. The extracted organic layer was washed saturated brine and aqueous sodium bicarbonate, dried over anhydrous sodium sulfate, filtrated and concentrated to give methyl 2-[4-[(2-ethyl-5,7-dimethylimidazo[4,5-b]pyridin-3-yl)methyl]phenyl]-2-methanesulfonyloxyacetate (8.4 g) in an amorphous form. The obtained residue was purified by silica gel column chromatography (hexane-ethyl acetate:3-1 v/v) to give the object compound (23.4 g) in an amorphous form.

A solution of methyl 2-[4-[(2-ethyl-5,7-dimethylimidazo[4,5-b]pyridin-3-yl)methyl]phenyl]-2-methanesulfonyloxyacetate (8.4 g) and thiourea (2.95 g) in ethanol (90 ml) was stirred under reflux for 30 min. The reaction mixture was concentrated under reduced pressure and ethyl acetate and water were added to allow precipitation of 5-[4-[(2-ethyl-5,7-dimethylimidazo[4,5-b]pyridin-3-yl)methyl]phenyl]-2-iminothiazolidin-4-one (6.23 g) as crystals.

To a suspension of 5-[4-[(2-ethyl-5,7-dimethylimidazo[4,5-b]pyridin-3-yl)methyl]phenyl]-2-iminothiazolidin-4-one (6.23 g) in ethanol was added concentrated hydrochloric acid (20 ml) to give a solution, which was stirred under reflux for 24 hrs. After the reaction, the mixture was concentrated under reduced pressure and the residue was dissolved in ethyl acetate-water, and the solution was neutralized with aqueous sodium bicarbonate. After partitioning and extraction, the extracted organic layer was washed with saturated brine, dried over anhydrous sodium sulfate, filtrated and concentrated, and the precipitated object compound (5.32 g) was collected by filtration melting point: 221-222° C.

$^1$H NMR (DMSO-$d_6$, 400 MHz): δ1.24 (3H, t, J=7.5 Hz), 2.49 (3H, s), 2.50 (3H, s), 2.78 (2H, q, J=7.5 Hz), 5.46 (2H, s), 5.77 (1H, s), 5.77 (1H, s), 6.95 (1H, s), 7.13 (2H, d, J=8.5 Hz), 7.37 (2H, d, J=8.5 Hz), 12.27 (1H, bs).

MS (FAB) M/z: 381 (M+H)$^+$.

Example 19

5-[4-[(5,7-dimethyl-2-propylimidazo[4,5-b]pyridin-3-yl)methyl]phenyl]-1,3-thiazolidine-2,4-dione (Example Compound No. 2-12)

By the reaction and work-up according to Examples 18a, 18b and 18c, the object compound was obtained from 5,7-dimethyl-2-propylimidazo[4,5-b]pyridine.

$^1$H NMR (DMSO-$d_6$, 400 MHz): δ0.91 (3H, t, J=7.5 Hz), 1.71 (2H, m), 2.49 (3H, s), 2.51 (3H, s), 2.74 (2H, t, J=7.5 Hz), 5.47 (2H, s), 5.77 (1H, s), 6.94 (1H, s), 7.13 (2H, d, J=8.0 Hz), 7.37 (2H, d, J=8.0 Hz), 12.28 (1H, bs).

Example 20

5-[2-[4-[(2-ethyl-5,7-dimethyl)imidazo[4,5-b]pyridin-3-yl)methyl]phenyl]phenyl]thiazolidine-2,4-dione (Example Compound No. 2-3)

By the reaction and work-up according to Examples 18a, 18b and 18c, the object compound was obtained from 2-ethyl-5,7-dimethylimidazo[4,5-b]pyridine and methyl 2-[2-[4-(bromomethyl)phenyl]phenyl]-2-oxoacetate.

melting point: 152-153° C.

$^1$H NMR (DMSO-$d_6$, 400 MHz): δ1.28 (3H, t, J=7.5 Hz), 2.52 (6H, s), 2.83 (2H, q, J=7.5 Hz), 5.52 (2H, s), 5.54 (1H, s), 6.95 (1H, s), 7.21-7.51 (9H, m)

Example 21 ethyl 3-[N-[4-(2,4-dioxothiazolidin-5-yl)benzyl]-N-pentanoylamino]benzoate (Example Compound No. 3-31)

(21a) methyl 2-[4-[(3-ethoxycarbonylphenylamino) methyl]phenyl]-2-oxoacetate

To a solution of ethyl 3-aminobenzoate (7.3 ml) and methyl 2-[4-(bromomethyl)phenyl]-2-oxoacetate (6.4 g) in dioxane (40 ml) was added diisopropylethylamine (6.4 ml), and the mixture was stirred at 60° C. for 2 hrs. The mixture was allowed to return to room temperature and toluene (330 ml) was added. The mixture was left standing at 0° C. for 5 hrs and the precipitated diisopropylethylamine hydrobromide was filtered off. The filtrate was concentrated under reduced pressure, and the residue was dissolved in ethyl acetate and water. The ethyl acetate layer was separated, washed with water, dried over anhydrous magnesium sulfate, and concentrated under reduced pressure. The residue was subjected to silica gel column chromatography (hexane-ethyl acetate:4-1 v/v) to give the object compound (7.61 g) as a syrup.

(21b) methyl 2-[4-[N-(3-ethoxycarbonylphenyl)-N-pentanoylamino]methyl]phenyl-2-oxoacetate To a solution of methyl 2-[4-[(3-ethoxycarbonylphenylamino)methyl]phenyl]-2-oxoacetate (0.75 g) obtained in 21a and pyridine (0.18 ml) in dichloromethane (7.5 ml) was added dropwise at 0° C. to 5° C. a solution of pentanoyl chloride (0.27 g) in dichloromethane (7.5 ml). The mixture was stirred at room temperature for 1 hr, concentrated, and the residue was dissolved in ethyl acetate. The ethyl acetate solution was washed successively with dilute hydrochloric acid, aqueous sodium bicarbonate and brine, dried over anhydrous magnesium sulfate and concentrated under reduced pressure to give the object compound (4.2 g) as a syrup.

(21c) methyl 2-[4-[N-(3-ethoxycarbonylphenyl)-N-pentanoylamino]methyl]phenyl-2-hydroxyacetate To a solution of methyl 2-[4-[N-(3-ethoxycarbonylphenyl)-N-pentanoylamino]methyl]phenyl-2-oxoacetate (7.00 g) obtained in 21b in methanol (35 ml) was added sodium borohydride (0.16 g) at –30° C. to –35° C. over 4 hrs. After the reaction, the reaction mixture was concentrated under reduced pressure, the residue was dissolved in ethyl acetate and water, and the ethyl acetate layer was separated. The extract was dried over anhydrous magnesium sulfate, and concentrated under reduced pressure to give the object compound (4.20 g) as a syrup.

(21d) methyl 2-[4-[N-(3-ethoxycarbonylphenyl)-N-pentanoylamino]methyl]phenyl-2-methanesulfonyloxyacetate To a solution of methyl 2-[4-[N-(3-ethoxycarbonylphenyl)-N-pentanoylamino]methyl]phenyl-2-hydroxyacetate (4.20 g) obtained in 21c and triethylamine (1.60 ml) in dichloromethane (42 ml) was added dropwise under ice-cooling a solution of methanesulfonyl chloride (0.90 ml) in dichloromethane (9 ml). The mixture was stirred at 0° C. to 5° C. for 2 hrs, and the reaction mixture was concentrated. The residue was dissolved in ethyl acetate, and the solution was washed with brine and dried over anhydrous magnesium sulfate. The extract was concentrated under reduced pressure to give the object compound (5.0 g) as a syrup.

(21e) ethyl 3-[N-[4-(2-imino-4-oxothiazolidin-5-yl)benzyl]-N-pentanoylamino]benzoate A mixed solution of methyl 2-[4-[N-(3-ethoxycarbonylphenyl)-N-pentanoylamino]methyl]phenyl-2-methanesulfonyloxyacetate (5.00 g) obtained in 21d and thiourea (1.60 g) in ethanol (50 ml) and dichloromethane (7 ml) was stirred at room temperature for 17 hrs. The reaction mixture was concentrated under reduced pressure, and ethyl acetate and aqueous sodium bicarbonate were added to allow precipitation of the object compound as crystals, which were collected by filtration and dried yield 3.1 g.

(21f) ethyl 3-[N-[4-(2,4-dioxothiazolidin-5-yl)benzyl]-N-pentanoylamino]benzoate Ethyl 3-[N-[4-(2-imino-4-oxothiazolidin-5-yl)benzyl]-N-pentanoylamino]benzoate (1.00 g) obtained in 21e was stirred in concentrated hydrochloric acid (0.5 ml) and ethanol (5 ml) at 65° C. for 15 hrs. The reaction mixture was concentrated under reduced pressure, the residue was dissolved in ethyl acetate, and the solution was neutralized with aqueous sodium bicarbonate. The ethyl acetate layer was separated, washed with brine, dried over anhydrous magnesium sulfate, and concentrated under reduced pressure. The residue was subjected to silica gel column chromatography (hexane-ethyl acetate:7-3v/v) to give the object compound (0.85 g) as a solid foam.

MS (FAS) M/z: 455 (M+H)$^+$.

$^1$H NMR (CDCl$_3$, 400 MHz): δ0.81 (3H, t, J=7.5 Hz), 1.20-1.31 (2H, m), 1.39 (3H, t, J=7.0 Hz), 1.55-1.61 (2H, m), 2.06 (2H, t, J=7.5 Hz), 4.38 (2H, q, J=7.0 Hz), 4.86 (1H, d, J=4.5 Hz), 4.94 (1H, d, J=4.5 Hz), 5.34 (1H, s), 7.11 (1H, d, J=7.5 Hz), 7.24-7.26 (2H, m), 7.33 (2H, d, J=8.0 Hz), 7.41 (1H, t, J=8.0 Hz), 7.74 (1H, s), 8.01 (1H, d, J=8.0 Hz), 8.70 (1H, s).

Example 22

3-[N-[4-(2,4-dioxothiazolidin-5-yl)benzyl]-N-pentanoylamino]benzoic acid (Example Compound No. 3-30)

To a solution ethyl 3-[N-[4-(2,4-dioxothiazolidin-5-yl)benzyl]-N-pentanoylamino]benzoate (0.73 g) obtained in Example 21f in ethanol (10 ml) was added 1N NaOH aqueous solution (3.5 ml), and the mixture was stirred at room temperature for 3 hrs. Then 1N NaOH aqueous solution (1.0 ml) was added, and the mixture was further stirred at room temperature for 3 hrs. To the reaction mixture was added 1N hydrochloric acid (4.5 ml), and the resultant product was extracted with ethyl acetate. The extract was dried over anhydrous magnesium sulfate and concentrated under reduced pressure. The residue was subjected to ODS column chromatography [water containing 1% acetic acid and acetonitrile (1:1)] to give the title compound (0.51 g) as a powder.

MS (FAS) M/z: 427 (M+H)$^+$.

$^1$H NMR (CDCl$_3$, 400 MHz): δ0.88 (3H, t, J=6.5 Hz), 1.19-1.30 (2H, m), 1.54-1.65 (2H, m), 2.08 (2H, t, J=7.5 Hz), 4.91 (2H, s), 5.34 (1H, s), 7.22-7.34 (3H, m), 7.33 (2H, d, J=8.0 Hz), 7.48 (1H, t, J=8.0 Hz), 7.65 (1H, s), 8.05 (1H, d, J=8.0 Hz), 9.51 (1H, s).

Experimental Example 1

AGEs Formation Inhibitory Effect

A solution (50 μl) of the test compound (final concentration 5 mM) in dimethyl sulfoxide was added to a protein (450 μl, serum of kidney failure patients who gave informed consent), and the mixture was incubated at 37° C. for one week. Pentosidine, which is one of the AGEs produced, was measured as follows. To separate pentosidine produced in the protein, 10% trichloroacetic acid (50 μl) was added to the sample after the reaction (50 μl) and the mixture was centrifuged and the precipitated protein was recovered. The recovered protein was washed with 300 μl of 5% trichloroacetic acid, dried and hydrolyzed with 6N hydrochloric acid (100 μl) at 110° C. for 16 hrs. The amount (nmol/l) of pentosidine produced was measured by HPLC (ODS C18, 4.6×250 mm, 335 nm, 385 nm) using a fluorescence detector by the gradient of 30 min., 1.0 ml/min with 0.1% trifluoroacetic acid added distilled water/0.08% trifluoroacetic acid added 80% acetonitrile as a mobile phase (Miyata, T et al.: J. Am. Soc. Nephrol., 7, 1198-1206, 1996, and Miyata, T. et al.: Proc. Natl. Acad. Sci. USA, 93 2353-2358, 1996).

To study AGEs formation inhibitory effect, the proportion of the aforementioned pentosidine production amount to the pentosidine production amount by control was calculated as pentosidine production rate (%). The results are shown in Table 4. Every test compound showed a pentosidine production inhibitory action.

TABLE 4

| Example No. | pentosidine production rate (%) |
|---|---|
| Example 1 | 18.1 |
| Example 2 | 26.1 |
| Example 3 | 21.3 |
| Example 4 | 17.4 |
| Example 5 | 9.33 |
| Example 6 | 16.8 |
| Example 7 | 27.2 |
| Example 8 | 23.5 |

TABLE 4-continued

| Example No. | pentosidine production rate (%) |
|---|---|
| Example 9 | 30.8 |
| Example 10 | 18.0 |
| Example 11 | 24.9 |
| Example 12 | 29.0 |
| Example 13 | 45.4 |
| Example 14 | 22.1 |
| Example 15 | 23.8 |
| Example 16 | 25.8 |
| Example 17 | 35.0 |
| Example 18 | 18.0 |
| Example 19 | 23.8 |
| Example 22 | 12.4 |

Pentosidine is one of the AGEs structures, and since the compound of the present invention inhibits pentsidine production, the compound has been clarified to have an AGEs formation inhibitory effect.

Due to the AGEs formation inhibitory activity, the compound of the present invention is useful for the treatment of diabetic complications (particularly diabetic nephropathy).

Formulation Example 1

| capsule | |
|---|---|
| compound of Example 1 | 10 mg |
| lactose | 110 mg |
| cornstarch | 58 mg |
| magnesium stearate | 2 mg |
| total | 180 mg |

The powders of respective components mentioned above were mixed thoroughly, and the mixture is passed through a 60 mesh sieve (standard of mesh: Tyler standard). The obtained powder (180 mg) is measured, filled in a gelatin capsule (No. 3) to give capsules.

Formulation Example 2

| tablet | |
|---|---|
| compound of Example 11 | 10 mg |
| lactose | 85 mg |
| cornstarch | 34 mg |
| microcrystalline cellulose | 20 mg |
| magnesium stearate | 1 mg |
| total | 150 mg |

The powders of respective components mentioned above were mixed thoroughly, and the mixture is compression formed to give tablets each weighing 150 mg. Where necessary, the tablets may be coated with sugar or a film.

Formulation Example 3

| granule | |
|---|---|
| compound of Example 14 | 10 mg |
| lactose | 839 mg |
| cornstarch | 150 mg |
| hydroxypropylcellulose | 1 mg |
| total | 1000 mg |

The powders of respective components mentioned above are mixed thoroughly, and the mixture is wetted with pure water, granulated in a basket-type granulator and dried to give granules.

INDUSTRIAL APPLICABILITY

The compound represented by the above-mentioned formula (I) of the present invention, which is the active ingredient, and a pharmacologically acceptable salt thereof and an ester thereof have a superior AGEs formation inhibitory effect, and are useful as agents for the prophylaxis or treatment of (particularly an agent for the treatment) diabetic complications (particularly nephropathy).

This application is based on a patent application No. 2003-340007 filed in Japan, the contents of which are hereby incorporated by reference.

The invention claimed is:

1. A compound represented by the formula (I)

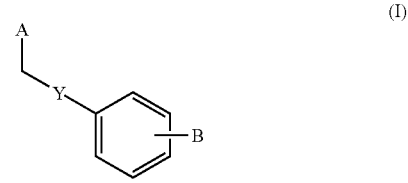

wherein
A is a group represented by the following formula (A2)

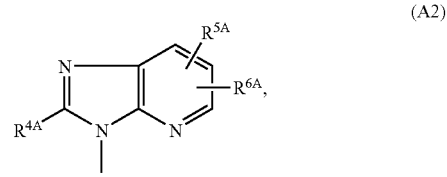

B is a 2,4-dioxothiazolidin-5-yl group,
Y is a single bond or a C6-10 arylene group,
$R^{4A}$, $R^{5A}$ and $R^{6A}$ are the same or different and each is a hydrogen atom or a C1-6 alkyl group, and
or a pharmacologically acceptable salt thereof or a carboxylate ester thereof.

2. The compound of claim 1, wherein Y is a C6-10 arylene group, or a pharmacologically acceptable salt thereof or a carboxylate ester thereof.

3. The compound of claim 1, wherein Y is a phenylene group, or a pharmacologically acceptable salt thereof or a carboxylate ester thereof.

4. The compound

5-[4-[(2-ethyl-5,7-dimethylimidazo[4,5-b]pyridin-3-yl)methyl]phenyl]-1,3-thiazolidine-2,4-dione, or a pharmacologically acceptable salt thereof or a carboxylate ester thereof.

5. A pharmaceutical composition comprising (a) the compound of claim 1, or a pharmacologically acceptable salt thereof or a carboxylate ester thereof, and (b) a carrier therefor.

6. A pharmaceutical composition comprising (a) the compound of claim 2, or a pharmacologically acceptable salt thereof or a carboxylate ester thereof, and (b) a carrier therefor.

7. A pharmaceutical composition comprising (a) the compound of claim 3, or a pharmacologically acceptable salt thereof or a carboxylate ester thereof, and (b) a carrier therefor.

8. A method of treating diabetic nephropathy by inhibiting AGEs formation in a warm-blooded animal, which comprises administering a pharmacological effective amount of the compound of claim 1, or a pharmacologically acceptable salt thereof or a carboxylate ester thereof, to the warm-blooded animal, whereupon diabetic nephropathy is treated.

9. The compound of claim 2, wherein Y is a phenylene group, or a pharmacologically acceptable salt thereof or a carboxylate ester thereof.

10. A pharmaceutical composition comprising (a) the compound of claim 9, or a pharmacologically acceptable salt thereof or a carboxylate ester thereof, and (b) a carrier therefor.

11. A pharmaceutical composition comprising (a) the compound of claim 4, or a pharmacologically acceptable salt thereof or a carboxylate ester thereof, and (b) a carrier therefor.

12. A method of treating diabetic nephropathy by inhibiting AGEs formation in a warm-blooded animal, which comprises administering a pharmacological effective amount of the compound of claim 2, or a pharmacologically acceptable salt thereof or a carboxylate ester thereof, to the warm-blooded animal, whereupon diabetic nephropathy is treated.

13. A method of treating diabetic nephropathy by inhibiting AGEs formation in a warm-blooded animal, which comprises administering a pharmacological effective amount of the compound of claim 4, or a pharmacologically acceptable salt thereof or a carboxylate ester thereof, to the warm-blooded animal, whereupon diabetic nephropathy is treated.

* * * * *